(12) United States Patent
Bujupi et al.

(10) Patent No.: US 11,851,463 B2
(45) Date of Patent: *Dec. 26, 2023

(54) CORE DOMAIN OF ANNEXINS AND USES THEREOF IN ANTIGEN DELIVERY AND VACCINATION

(71) Applicant: Deutsches Krebsforschungszentrum Stiftung des öffentlichen Rechts, Heidelberg (DE)

(72) Inventors: Fatmire Bujupi, Heidelberg (DE); Peter Krammer, Heidelberg (DE); Heiko Weyd, Mannheim (DE)

(73) Assignee: DEUTSCHES KREBSFORSCHUNGSZENTRUM STIFTUNG DES ÖFFENTLICHEN RECHTS, Heidelberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/154,477

(22) Filed: Jan. 21, 2021

(65) Prior Publication Data

US 2021/0230238 A1 Jul. 29, 2021

Related U.S. Application Data

(63) Continuation of application No. 16/308,702, filed as application No. PCT/EP2017/063985 on Jun. 8, 2017, now Pat. No. 10,947,283.

(30) Foreign Application Priority Data

Jun. 10, 2016 (EP) .................................. 16173925

(51) Int. Cl.
| | |
|---|---|
| *C07K 14/47* | (2006.01) |
| *A61K 39/39* | (2006.01) |
| *A61K 47/64* | (2017.01) |
| *A61P 35/00* | (2006.01) |
| *C07K 14/74* | (2006.01) |
| *A61K 39/00* | (2006.01) |
| *A61K 38/00* | (2006.01) |

(52) U.S. Cl.
CPC .............. *C07K 14/47* (2013.01); *A61K 39/39* (2013.01); *A61K 47/646* (2017.08); *A61P 35/00* (2018.01); *C07K 14/70539* (2013.01); *A61K 38/00* (2013.01); *A61K 2039/572* (2013.01); *C07K 2319/00* (2013.01); *C07K 2319/30* (2013.01); *C07K 2319/33* (2013.01)

(58) Field of Classification Search
CPC ................................ C07K 14/47; A61K 39/39
See application file for complete search history.

(56) References Cited

U.S. PATENT DOCUMENTS

| | | | |
|---|---|---|---|
| 2002/0052358 A1 | 5/2002 | Chubinskaya et al. | |
| 2006/0286074 A1* | 12/2006 | Tang | C07K 14/705 435/456 |
| 2009/0324575 A1* | 12/2009 | Shayman | C12Y 203/01 435/375 |
| 2012/0121571 A1* | 5/2012 | Shayman | A61P 37/00 424/94.6 |
| 2012/0251453 A1* | 10/2012 | Fukuda | A61P 43/00 424/9.1 |
| 2013/0331546 A1* | 12/2013 | Ohlfest | A61K 51/087 530/350 |
| 2014/0322214 A1 | 4/2014 | Banchereau et al. | |
| 2016/0279212 A1* | 9/2016 | Ohlfest | A61K 39/0011 |

FOREIGN PATENT DOCUMENTS

| | | | |
|---|---|---|---|
| EP | 3045470 | 7/2016 | |
| JP | 2014-095643 | 5/2014 | |
| WO | 01/10199 | 2/2001 | |
| WO | 02/17857 | 3/2002 | |
| WO | 2005/027965 | 3/2005 | |
| WO | 2006/130525 | 12/2006 | |
| WO | 2009/049892 | 4/2009 | |
| WO | 2014/126127 | 8/2014 | |
| WO | WO 2015/073632 | * 5/2015 | ............. A61K 39/39 |

OTHER PUBLICATIONS

Andersen et al., Feb. 16, 2016, Monomeric annexin A2 is an oxygen-regulated toll-like receptor 2 ligand and adjuvant, Journal of ImmunoTherapy of Cancer, 4(11): (8 pages).*
Kukutsch et al., 2000, Formation and Kinetics of MHC Class I-Ovalbumin Peptide Complexes on Immature and Mature Murine Dendritic Cells, J Invest Dermatol, 115: 449-453.*
International Search Report and Written Opinion, International Patent Application No. PCT/EP2017/063985, dated Sep. 25, 2017 (18 pages).
Linke et al., "The Tolerogenic Function of Annexins on Apoptotic Cells is Mediated by the Annexin Core Domain", The Journal of Immunology, vol. 194, No. 11, Apr. 27, 2015, pp. 5233-5242.
Tzelepis et al., "Annexin1 regulates DC efferocytosis and cross-presentation during *Mycobacterium tuberculosis* infection", Journal Clinical Investigation, vol. 125, No. 2, Dec. 22, 2014, pp. 752-768.

\* cited by examiner

*Primary Examiner* — Amber D Steele

(74) *Attorney, Agent, or Firm* — Hamre, Schumann, Mueller & Larson, P.C.

(57) ABSTRACT

The present disclosure provides immunogenic compositions, such as vaccines, including DNA vaccines, and uses thereof, e.g., which include an annexin core domain to mediate efficient antigen delivery and antigen presentation in order to induce an antigen-specific immune response and/or to treat or prevent infectious diseases and/or cancer.

11 Claims, 16 Drawing Sheets

Specification includes a Sequence Listing.

Figure 8 hANXA1 → gi|47115305|emb|CAG28612.1|   MAMVSEFLKQAWFIENEEQEYVQTVKSSKGGPGSAVSPYPTFNPSSDVAALHKAIMVKGV
hANXA5 → gi|49456639|emb|CAG46640.1|   ----------------------------MAQVLRGTVTDFPGFDERADAETLRKAMKGLGT
hANXA13 → gi|49456633|emb|CAG46637.1|  ---------------------------MGNRHAKASSPQGFDVERDAKKLNKACKGMGT
                                                                          :  :

gi|47115305|emb|CAG28612.1|   DEATIIDILTKRNNAQRQQIKAAYLQETGKPLDETLKKALTGHLEEVVLALLKTPAQFDA
gi|49456639|emb|CAG46640.1|   DEESILTLLTSRSNAQRQEISAAFKTLFGRDLLDDLKSELTGKFEKLIVALMKPSRLYDA
gi|49456633|emb|CAG46637.1|   NEAAIIEILSGRTSDERQQIKQKYKATYGKELIEEVLSELSGNFEKTALALLDHPSEYAA
                                 :  :  :      *:: ::: :    . *   :: *.  *. : :   *   ::

gi|47115305|emb|CAG28612.1|   DELRAAMKGLGTDEDTLIEILASRTNKEIRDINRVYREELKRDLAKDITSDTSGDFRNAL
gi|49456639|emb|CAG46640.1|   YELKHALKGAGTNEKVLTEIIASRTPEELRAIKQVYEEEYGSSLEDDVVGDTSGYYQRML
gi|49456633|emb|CAG46637.1|   RQLQKAMKGLGTDESVLIEVLCTRTNKEIIAIKEAYQRLFDRSLESDVKGDTSGNLKKIL
                                 :.:.:: *.*: ::*.   :: : . *  :  .  *.. . .****  :::

gi|47115305|emb|CAG28612.1|   LSLAKGDRSEDFGVNEDLADSDARALYEAGERRKGTDVNVFNTILTTRSYPQLRRVFQKY
gi|49456639|emb|CAG46640.1|   VVLLQANRDPDAGIDEAQVEQDAQALFQAGELKWGTDEEKFITIFGTRSVSHLRKVFDKY
gi|49456633|emb|CAG46637.1|   VSLLQANRNEGDDVDKDLAGQDANDLYDAGEGRWGTDEVAFNEVLAKRSYKQLRATFQAY
                              :  :  .   .   :     *  .*:     .*    *   :. **  *: * ** gi|47115305|emb|CAG28612.1|   TKYSKHDMNKVLDLELKGDIERCLTAIVKCATSKPAFFAEKLHQAMKGVGTRHKALIRIM
gi|49456639|emb|CAG46640.1|   MTISGFQIEETIDRETSGNLEQLLLAVVKSISPAYLAETLYYAMKGAGTDDHTLIRVM
gi|49456633|emb|CAG46637.1|   QILIGKDIEEAIEEETSGDLQKAYLTLVPCAQDCEDYFAERLYKSMKGAGTDEETLIRII
                                : . :   :  ::   .  : :  .*. .    * .:: ::.. .. **::

gi|47115305|emb|CAG28612.1|   VSRSEIDMNDIKAFYQKMYGISLCQAILDETKGDYEKILVALCGGN---
gi|49456639|emb|CAG46640.1|   VSRSEIDLFNIRKEFRKNFATSLYSMIKGDTSGDYKKALLLCGGEDD---
gi|49456633|emb|CAG46637.1|   VTRAEVDLLQGIKAKFQEKYQKSLSDMVRSDTSGDFRKLLVALLH----
                              *:*:*:*   * : ::: .  ** .::. . .*: :: ::

A) Anx-OVA fusionprotein, DNA-sequence

ATGAATCCATCCTCGGATGTCGCTGCCTTGCATAAGGCCATAATGGTTAAAGGTGTGGATGAGGCAACCATCATT
GACATTCTAACTAAGCGAAACAATGCACAGCGTCAACAGATCAAAGCAGCATATCTCCAGGAAACAGGAAAGCCC
CTGGATGAAACACTGAAGAAAGCCCTTACAGGTCACCTTGAGGAGGTTGTTTTAGCTCTGCTAAAAACTCCAGCG
CAATTTGATGCTGATGAACTTCGTGCTGCCATGAAGGGCCTTGGAACTGATGAAGATACTCTAATTGAGATTTTG
GCATCAAGAACTAACAAAGAAATCAGAGACATTAACAGGGTCTACAGAGAGGAACTGAAGAGAGATCTGGCCAA
AGACATAACCTCAGACACATCTGGAGATTTTCGGAACGCTTTGCTTTCTCTTGCTAAGGGTGACCGATCTGAGGA
CTTTGGTGTGAATGAAGACTTGGCTGATTCAGATGCCAGGGCCTTGTATGAAGCAGGAGAAAGGAGAAAGGGGA
CAGACGTAAACGTGTTCAATACCATCCTTACCACCAGAAGCTATCCACAACTTCGCAGAGTGTTTCAGAAATACAC
CAAGTACAGTAAGCATGACATGAACAAAGTTCTGGACCTGGAGTTGAAAGGTGACATTGAGAAATGCCTCACAGC
TATCGTGAAGTGCGCCACAAGCAAACCAGCTTTCTTTGCAGAGAAGCTTCATCAAGCCATGAAAGGTGTTGGAAC
TCGCCATAAGGCATTGATCAGGATTATGGTTTCCCGTTCTGAAATTGACATGAATGATATCAAAGCATTCTATCA
GAAGATGTATGGTATCTCCCTTTGCCAAGCCATCCTGGATGAAACCAAAGGAGATTATGAGAAAATCCTGGTGGC
TCTTTGTGGAGGAAACcatcggggatccggcggaggttcaggcggaggttcagaaaacttgtatttccagggcggcggaggttcaggcggaggttc- GATCAAGCCAGAGAGCTCATCAATTCCTGGGTAGAAAGTCAGACAAATGGAATTATCAGAAATGTCCTTCAGCCA
AGCTCCGTGGATTCTCAAACTGCAATGGTTCTGGTTAATGCCATTGTCTTCAAAGGACTGTGGGAGAAAGCATTT
AAGGATGAAGACACACAAGCAATGCCTTTCAGAGTGACTGAGCAAGAAAGCAAACCTGTGCAGATGATGTACCAG
ATTGGTTTATTTAGAGTGGCATCAATGGCTTCTGAGAAAATGAAGATCCTGGAGCTTCCATTTGCCAGTGGGACA
ATGAGCATGTTGGTGCTGTTGCCTGATGAAGTCTCAGGCCTTGAGCAGCTTGAGAGTATAATCAACTTTGAAAAA
CTGACTGAATGGACCAGTTCTAATGTTATGGAAGAGAGGAAGATCAAAGTGTACTTACCTCGCATGAAGATGGA
GGAAAAATACAACCTCACATCTGTCTTAATGGCTATGGGCATTACTGACGTGTTTAGCTCTTCAGCCAATCTGTC
TGGCATCTCCTCAGCAGAGAGCCTGAAGATATCTCAAGCTGTCCATGCAGCACATGCAGAAATCAATGAAGCAGG
CAGAGAGGTGGTAGGGTCAGCAGAGGCTGGAGTGGATGCTGCAAGCGTCTCTGAAGAATTTAGGGCTGACCATCC
ATTCCTCTTCTGTATCAAGCACATCGCAACCAACGCCGTTCTCTTCTTTGGCAGATGTGTTTCCCCT

Figure 10B

B) Anx-OVA fusionprotein, aminoacid-sequence

MNPSSDVAALHKAIMVKGVDEATIIDILTKRNNAQRQQIKAAYLQETGKPLDETLKKALTGHLEEVVLALLKTPAQ
FDADELRAAMKGLGTDEDTLIEILASRTNKEIRDINRVYREELKRDLAKDITSDTSGDFRNALLSLAKGDRSEDFGV
NEDLADSDARALYEAGERRKGTDVNVFNTILTTRSYPQLRRVFQKYTKYSKHDMNKVLDLELKGDIEKCLTAIVKC
ATSKPAFFAEKLHQAMKGVGTRHKALIRIMVSRSEIDMNDIKAFYQKMYGISLCQAILDETKGDYEKILVALCGGN-

HRGSGGGSGGGSENLYFQGGGGSGGGS-

DQARELINSWVESQTNGIIRNVLQPSSVDSQTAMVLVNAIVFKGLWEKAFKDEDTQAMPFRVTEQESKPVQMMYQ
IGLFRVASMASEKMKILELPFASGTMSMLVLLPDEVSGLEQLESIINFEKLTEWTSSNVMEERKIKVYLPRMKMEEK
YNLTSVLMAMGITDVFSSSANLSGISSAESLKISQAVHAAHAEINEAGREVVGSAEAGVDAASVSEEFRADHPFLFCIK
HIATNAVLFFGRCVSP huAnxA1 Core flexible Linker ovalbumin (OVA)

SEQUENCE LISTING

```
<160> NUMBER OF SEQ ID NOS: 15

<210> SEQ ID NO 1
<211> LENGTH: 346
<212> TYPE: PRT
<213> ORGANISM: Homo sapiens

<400> SEQUENCE: 1

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
        35                  40                  45

Ala Ala Leu His Lys Ala Ile Met Val Lys Gly Val Asp Glu Ala Thr
    50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
            100                 105                 110

Lys Thr Pro Ala Gln Phe Asp Ala Asp Glu Leu Arg Ala Ala Met Lys
        115                 120                 125

Gly Leu Gly Thr Asp Glu Asp Thr Leu Ile Glu Ile Leu Ala Ser Arg
    130                 135                 140

Thr Asn Lys Glu Ile Arg Asp Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Asn Ala Leu Leu Ser Leu Ala Lys Gly Asp Arg Ser Glu Asp Phe
            180                 185                 190

Gly Val Asn Glu Asp Leu Ala Asp Ser Asp Ala Arg Ala Leu Tyr Glu
        195                 200                 205

Ala Gly Glu Arg Arg Lys Gly Thr Asp Val Asn Val Phe Asn Thr Ile
    210                 215                 220

Leu Thr Thr Arg Ser Tyr Pro Gln Leu Arg Arg Val Phe Gln Lys Tyr
225                 230                 235                 240

Thr Lys Tyr Ser Lys His Asp Met Asn Lys Val Leu Asp Leu Glu Leu
                245                 250                 255

Lys Gly Asp Ile Glu Lys Cys Leu Thr Ala Ile Val Lys Cys Ala Thr
            260                 265                 270

Ser Lys Pro Ala Phe Phe Ala Glu Lys Leu His Gln Ala Met Lys Gly
        275                 280                 285

Val Gly Thr Arg His Lys Ala Leu Ile Arg Ile Met Val Ser Arg Ser
    290                 295                 300

Glu Ile Asp Met Asn Asp Ile Lys Ala Phe Tyr Gln Lys Met Tyr Gly
305                 310                 315                 320

Ile Ser Leu Cys Gln Ala Ile Leu Asp Glu Thr Lys Gly Asp Tyr Glu
                325                 330                 335
```

```
Lys Ile Leu Val Ala Leu Cys Gly Gly Asn
            340                 345

<210> SEQ ID NO 2
<211> LENGTH: 320
<212> TYPE: PRT
<213> ORGANISM: Homo sapiens

<400> SEQUENCE: 2

Met Ala Gln Val Leu Arg Gly Thr Val Thr Asp Phe Pro Gly Phe Asp
1               5                   10                  15

Glu Arg Ala Asp Ala Glu Thr Leu Arg Lys Ala Met Lys Gly Leu Gly
            20                  25                  30

Thr Asp Glu Glu Ser Ile Leu Thr Leu Leu Thr Ser Arg Ser Asn Ala
        35                  40                  45

Gln Arg Gln Glu Ile Ser Ala Ala Phe Lys Thr Leu Phe Gly Arg Asp
    50                  55                  60

Leu Leu Asp Asp Leu Lys Ser Glu Leu Thr Gly Lys Phe Glu Lys Leu
65                  70                  75                  80

Ile Val Ala Leu Met Lys Pro Ser Arg Leu Tyr Asp Ala Tyr Glu Leu
                85                  90                  95

Lys His Ala Leu Lys Gly Ala Gly Thr Asn Glu Lys Val Leu Thr Glu
            100                 105                 110

Ile Ile Ala Ser Arg Thr Pro Glu Glu Leu Arg Ala Ile Lys Gln Val
        115                 120                 125

Tyr Glu Glu Glu Tyr Gly Ser Ser Leu Glu Asp Asp Val Val Gly Asp
    130                 135                 140

Thr Ser Gly Tyr Tyr Gln Arg Met Leu Val Val Leu Leu Gln Ala Asn
145                 150                 155                 160

Arg Asp Pro Asp Ala Gly Ile Asp Glu Ala Gln Val Glu Gln Asp Ala
                165                 170                 175

Gln Ala Leu Phe Gln Ala Gly Glu Leu Lys Trp Gly Thr Asp Glu Glu
            180                 185                 190

Lys Phe Ile Thr Ile Phe Gly Thr Arg Ser Val Ser His Leu Arg Lys
        195                 200                 205

Val Phe Asp Lys Tyr Met Thr Ile Ser Gly Phe Gln Ile Glu Glu Thr
    210                 215                 220

Ile Asp Arg Glu Thr Ser Gly Asn Leu Glu Gln Leu Leu Leu Ala Val
225                 230                 235                 240

Val Lys Ser Ile Arg Ser Ile Pro Ala Tyr Leu Ala Glu Thr Leu Tyr
                245                 250                 255

Tyr Ala Met Lys Gly Ala Gly Thr Asp Asp His Thr Leu Ile Arg Val
            260                 265                 270

Met Val Ser Arg Ser Glu Ile Asp Leu Phe Asn Ile Arg Lys Glu Phe
        275                 280                 285

Arg Lys Asn Phe Ala Thr Ser Leu Tyr Ser Met Ile Lys Gly Asp Thr
    290                 295                 300

Ser Gly Asp Tyr Lys Lys Ala Leu Leu Leu Leu Cys Gly Glu Asp Asp
305                 310                 315                 320

<210> SEQ ID NO 3
<211> LENGTH: 316
<212> TYPE: PRT
<213> ORGANISM: Homo sapiens

<400> SEQUENCE: 3
```

```
Met Gly Asn Arg His Ala Lys Ala Ser Ser Pro Gln Gly Phe Asp Val
1               5                   10                  15

Asp Arg Asp Ala Lys Lys Leu Asn Lys Ala Cys Lys Gly Met Gly Thr
            20                  25                  30

Asn Glu Ala Ala Ile Ile Glu Ile Leu Ser Gly Arg Thr Ser Asp Glu
        35                  40                  45

Arg Gln Gln Ile Lys Gln Lys Tyr Lys Ala Thr Tyr Gly Lys Glu Leu
    50                  55                  60

Glu Glu Val Leu Lys Ser Gly Leu Ser Gly Asn Phe Glu Lys Thr Ala
65                  70                  75                  80

Leu Ala Leu Leu Asp His Pro Ser Glu Tyr Ala Ala Arg Gln Leu Gln
                85                  90                  95

Lys Ala Met Lys Gly Leu Gly Thr Asp Glu Ser Val Leu Ile Glu Val
            100                 105                 110

Leu Cys Thr Arg Thr Asn Lys Glu Ile Ile Ala Ile Lys Glu Ala Tyr
        115                 120                 125

Gln Arg Leu Phe Asp Arg Ser Leu Glu Ser Asp Val Lys Gly Asp Thr
    130                 135                 140

Ser Gly Asn Leu Lys Lys Ile Leu Val Ser Leu Leu Gln Ala Asn Arg
145                 150                 155                 160

Asn Glu Gly Asp Asp Val Asp Lys Asp Leu Ala Gly Gln Asp Ala Lys
            165                 170                 175

Asp Leu Tyr Asp Ala Gly Glu Gly Arg Trp Gly Thr Asp Glu Leu Ala
        180                 185                 190

Phe Asn Glu Val Leu Ala Lys Arg Ser Tyr Lys Gln Leu Arg Ala Thr
    195                 200                 205

Phe Gln Ala Tyr Gln Ile Leu Ile Gly Lys Asp Ile Glu Glu Ala Ile
    210                 215                 220

Glu Glu Glu Thr Ser Gly Asp Leu Gln Lys Ala Tyr Leu Thr Leu Val
225                 230                 235                 240

Arg Cys Ala Gln Asp Cys Glu Asp Tyr Phe Ala Glu Arg Leu Tyr Lys
            245                 250                 255

Ser Met Lys Gly Ala Gly Thr Asp Glu Glu Thr Leu Ile Arg Ile Ile
        260                 265                 270

Val Thr Arg Ala Glu Val Asp Leu Gln Gly Ile Lys Ala Lys Phe Gln
    275                 280                 285

Glu Lys Tyr Gln Lys Ser Leu Ser Asp Met Val Arg Ser Asp Thr Ser
    290                 295                 300

Gly Asp Phe Arg Lys Leu Leu Val Ala Leu Leu His
305                 310                 315

<210> SEQ ID NO 4
<211> LENGTH: 8
<212> TYPE: PRT
<213> ORGANISM: Gallus gallus

<400> SEQUENCE: 4

Ser Ile Ile Asn Phe Glu Lys Leu
1               5

<210> SEQ ID NO 5
<211> LENGTH: 17
<212> TYPE: PRT
<213> ORGANISM: Gallus gallus

<400> SEQUENCE: 5
```

Ile Ser Gln Ala Val His Ala Ala His Ala Glu Ile Asn Glu Ala Gly
1               5                   10                  15

Arg

<210> SEQ ID NO 6
<211> LENGTH: 346
<212> TYPE: PRT
<213> ORGANISM: Mus musculus

<400> SEQUENCE: 6

Met Ala Met Val Ser Glu Phe Leu Lys Gln Ala Arg Phe Leu Glu Asn
1               5                   10                  15

Gln Glu Gln Glu Tyr Val Gln Ala Val Lys Ser Tyr Lys Gly Gly Pro
                20                  25                  30

Gly Ser Ala Val Ser Pro Tyr Pro Ser Phe Asn Val Ser Ser Asp Val
            35                  40                  45

Ala Ala Leu His Lys Ala Ile Met Val Lys Gly Val Asp Glu Ala Thr
        50                  55                  60

Ile Ile Asp Ile Leu Thr Lys Arg Thr Asn Ala Gln Arg Gln Gln Ile
65                  70                  75                  80

Lys Ala Ala Tyr Leu Gln Glu Asn Gly Lys Pro Leu Asp Glu Val Leu
                85                  90                  95

Arg Lys Ala Leu Thr Gly His Leu Glu Glu Val Val Leu Ala Met Leu
            100                 105                 110

Lys Thr Pro Ala Gln Phe Asp Ala Asp Glu Leu Arg Gly Ala Met Lys
        115                 120                 125

Gly Leu Gly Thr Asp Glu Asp Thr Leu Ile Glu Ile Leu Thr Thr Arg
130                 135                 140

Ser Asn Glu Gln Ile Arg Glu Ile Asn Arg Val Tyr Arg Glu Glu Leu
                145                 150                 155                 160

Lys Arg Asp Leu Ala Lys Asp Ile Thr Ser Asp Thr Ser Gly Asp Phe
            165                 170                 175

Arg Lys Ala Leu Leu Ala Leu Ala Lys Gly Asp Arg Cys Gln Asp Leu
        180                 185                 190

Ser Val Asn Gln Asp Leu Ala Asp Thr Asp Ala Arg Ala Leu Tyr Glu
    195                 200                 205

Ala Gly Glu Arg Arg Lys Gly Thr Asp Val Asn Val Phe Thr Thr Ile
210                 215                 220

Leu Thr Ser Arg Ser Phe Pro His Leu Arg Arg Val Phe Gln Asn Tyr
225                 230                 235                 240

Gly Lys Tyr Ser Gln His Asp Met Asn Lys Ala Leu Asp Leu Glu Leu
                245                 250                 255

Lys Gly Asp Ile Glu Lys Cys Leu Thr Thr Ile Val Lys Cys Ala Thr
            260                 265                 270

Ser Thr Pro Ala Phe Phe Ala Glu Lys Leu Tyr Glu Ala Met Lys Gly
        275                 280                 285

Ala Gly Thr Arg His Lys Ala Leu Ile Arg Ile Met Val Ser Arg Ser
    290                 295                 300

Glu Ile Asp Met Asn Glu Ile Lys Val Phe Tyr Gln Lys Tyr Gly
305                 310                 315                 320

Ile Ser Leu Cys Gln Ala Ile Leu Asp Glu Thr Lys Gly Asp Tyr Glu
                325                 330                 335

Lys Ile Leu Val Ala Leu Cys Gly Gly Asn
            340                 345

<210> SEQ ID NO 7
<211> LENGTH: 319
<212> TYPE: PRT
<213> ORGANISM: Mus musculus

<400> SEQUENCE: 7

Met Ala Thr Arg Gly Thr Val Thr Asp Phe Pro Gly Phe Asp Gly Arg
1               5                   10                  15

Ala Asp Ala Glu Val Leu Arg Lys Ala Met Lys Gly Leu Gly Thr Asp
            20                  25                  30

Glu Asp Ser Ile Leu Asn Leu Leu Thr Ser Arg Ser Asn Ala Gln Arg
        35                  40                  45

Gln Glu Ile Ala Gln Glu Phe Lys Thr Leu Phe Gly Arg Asp Leu Val
    50                  55                  60

Asp Asp Leu Lys Ser Glu Leu Thr Gly Lys Phe Glu Lys Leu Ile Val
65                  70                  75                  80

Ala Met Met Lys Pro Ser Arg Leu Tyr Asp Ala Tyr Glu Leu Lys His
                85                  90                  95

Ala Leu Lys Gly Ala Gly Thr Asp Glu Lys Val Leu Thr Glu Ile Ile
            100                 105                 110

Ala Ser Arg Thr Pro Glu Glu Leu Ser Ala Ile Lys Gln Val Tyr Glu
        115                 120                 125

Glu Glu Tyr Gly Ser Asn Leu Glu Asp Asp Val Val Gly Asp Thr Ser
    130                 135                 140

Gly Tyr Tyr Gln Arg Met Leu Val Val Leu Leu Gln Ala Asn Arg Asp
145                 150                 155                 160

Pro Asp Thr Ala Ile Asp Asp Ala Gln Val Glu Leu Asp Ala Gln Ala
                165                 170                 175

Leu Phe Gln Ala Gly Glu Leu Lys Trp Gly Thr Asp Glu Glu Lys Phe
            180                 185                 190

Ile Thr Ile Phe Gly Thr Arg Ser Val Ser His Leu Arg Arg Val Phe
        195                 200                 205

Asp Lys Tyr Met Thr Ile Ser Gly Phe Gln Ile Glu Glu Thr Ile Asp
    210                 215                 220

Arg Glu Thr Ser Gly Asn Leu Glu Gln Leu Leu Leu Ala Val Val Lys
225                 230                 235                 240

Ser Ile Arg Ser Ile Pro Ala Tyr Leu Ala Glu Thr Leu Tyr Tyr Ala
                245                 250                 255

Met Lys Gly Ala Gly Thr Asp Asp His Thr Leu Ile Arg Val Val Val
            260                 265                 270

Ser Arg Ser Glu Ile Asp Leu Phe Asn Ile Arg Lys Glu Phe Arg Lys
        275                 280                 285

Asn Phe Ala Thr Ser Leu Tyr Ser Met Ile Lys Gly Asp Thr Ser Gly
    290                 295                 300

Asp Tyr Lys Lys Ala Leu Leu Leu Leu Cys Gly Gly Glu Asp Asp
305                 310                 315

<210> SEQ ID NO 8
<211> LENGTH: 317
<212> TYPE: PRT
<213> ORGANISM: Mus musculus

<400> SEQUENCE: 8

Met Gly Asn Arg His Ala Lys Glu Arg Ser His His Gly Phe Asp
1               5                   10                  15

Ala Asp Arg Asp Ala Lys Lys Leu Tyr Lys Ala Cys Lys Gly Met Gly
            20                  25                  30

Thr Asp Glu Ala Ala Ile Ile Glu Val Leu Ser Ser Arg Thr Ser Glu
        35                  40                  45

Glu Arg Gln Gln Ile Lys Gln Lys Tyr Lys Lys Tyr Gly Lys Lys Asp
50                  55                  60

Leu Glu Glu Val Leu Asn Ser Glu Leu Ser Gly Asn Phe Lys Lys Thr
65                  70                  75                  80

Ala Leu Ala Leu Leu Asp Arg Pro Asn Glu Tyr Ala Ala Arg Gln Leu
                85                  90                  95

Gln Lys Ala Met Lys Gly Val Gly Thr Asp Glu Ala Met Leu Ile Glu
            100                 105                 110

Ile Leu Cys Thr Arg Ser Asn Lys Glu Ile Val Ala Ile Lys Glu Ala
            115                 120                 125

Tyr Gln Arg Leu Phe Gly Arg Ser Leu Glu Ser Asp Val Lys Glu Asp
            130                 135                 140

Thr Ser Gly Asn Leu Arg Lys Ile Leu Val Ser Leu Leu Gln Ala Ser
145                 150                 155                 160

Arg Asp Glu Glu Asp Thr Val Asp Lys Glu Leu Ala Gly Gln Asp Ala
            165                 170                 175

Lys Asp Leu Tyr Asp Ala Gly Glu Gly Arg Trp Gly Thr Asp Glu Leu
            180                 185                 190

Ala Phe Asn Glu Val Leu Ala Lys Arg Ser Tyr Lys Gln Leu Arg Ala
            195                 200                 205

Thr Phe Gln Ala Tyr Gln Ile Leu Ile Gly Lys Asp Met Glu Glu Thr
            210                 215                 220

Ile Glu Glu Glu Thr Ser Gly Asp Leu Lys Lys Ala Tyr Leu Thr Ile
225                 230                 235                 240

Val Arg Cys Ala Gln Asp Leu Glu Gly Tyr Phe Ala Asp Leu Leu Tyr
            245                 250                 255

Lys Ala Met Lys Gly Met Gly Thr Asp Glu Glu Thr Leu Ile Arg Ile
            260                 265                 270

Ile Val Thr Arg Ala Glu Val Asp Leu Gln Gly Ile Lys Ala Lys Phe
            275                 280                 285

Gln Glu Lys Tyr Gln Lys Ser Leu Ser Asp Met Val His Ser Asp Thr
290                 295                 300

Ser Gly Asp Phe Arg Lys Leu Leu Val Ala Leu Leu His
305                 310                 315

<210> SEQ ID NO 9
<211> LENGTH: 45
<212> TYPE: DNA
<213> ORGANISM: artificial
<220> FEATURE:
<223> OTHER INFORMATION: primer

<400> SEQUENCE: 9
ggcggaggtt caggcggagg ttcagatcaa gccagagagc tcatc      45

<210> SEQ ID NO 10
<211> LENGTH: 37
<212> TYPE: DNA
<213> ORGANISM: artificial
<220> FEATURE:
<223> OTHER INFORMATION: primer

<400> SEQUENCE: 10

```
gaaaacttgt atttccaggg cggcggaggt tcaggcg                              37
```

<210> SEQ ID NO 11
<211> LENGTH: 53
<212> TYPE: DNA
<213> ORGANISM: artificial
<220> FEATURE:
<223> OTHER INFORMATION: primer

<400> SEQUENCE: 11

```
ggatccggcg gaggttcagg cggaggttca gaaaacttgt atttccaggg cgg           53
```

<210> SEQ ID NO 12
<211> LENGTH: 28
<212> TYPE: DNA
<213> ORGANISM: artificial
<220> FEATURE:
<223> OTHER INFORMATION: primer

<400> SEQUENCE: 12

```
ggatccaggg gaaacacatc tgccaaag                                       28
```

<210> SEQ ID NO 13
<211> LENGTH: 1724
<212> TYPE: DNA
<213> ORGANISM: Artificial
<220> FEATURE:
<223> OTHER INFORMATION: Fusion Protein

<400> SEQUENCE: 13

```
atgaatccat cctcggatgt cgctgccttg cataaggcca taatggttaa aggtgtggat    60
gaggcaacca tcattgacat tctaactaag cgaaacaatg cacagcgtca acagatcaaa   120
gcagcattct ccaggaaaca ggaaagcccc tggatgaaac actgaagaaa gcccttacag   180
gtcaccttga ggaggttgtt ttagctctgc taaaaactcc agcgcaattt gatgctgatg   240
aacttcgtgc tgcctgaagg gccttggaac tgatgaagat actctaattg agattttggc   300
atcaagaact aacaaagaaa tcagagacat taacagggtc tacagagagg aactgaagag   360
agatctggcc aaagacataa ctcagacaca tctggagatt tcggaacgc tttgctttct   420
cttgctaagg gtgaccgatc tgaggacttt ggtgtgaatg aagacttggc tgattcagat   480
gccagggcct tgtatgaagc aggagaaaga gaaaggggac agacgtaaac gtgttcaata   540
ccatccttac caccagaagc tatccacaac ttcgcagagt gtttcagaaa tacaccaagt   600
acagtaagca tgcatgaac aaagttctgg acctgagttg aaaggtgaca ttgagaaatg   660
cctcacagct atcgtgaagt gcgccacaag caaaccagct ttctttgcag agaagcttca   720
tcaagccatg aaaggtgttg aactcgcca taggcattg ataggattat ggtttcccgt    780
tctgaaattg acatgaatga tatcaaagca ttctatcaga agatgtatgg tatctccctt   840
tgccaagcca tcctggatga aaccaaagga gattatgaga aaatcctggg gctctttgtg   900
gaggaaacca tcggggatcc ggcggaggtt caggcggagg ttcagaaaac ttgtatttcc   960
agggcggcgg aggttcaggc ggaggttcga tcagccaga gagctcatca attcctgggt  1020
agaaagtcag acaaatggaa ttatcagaaa tgtccttcag ccaagctccg tggattctca  1080
aactgcaatg gttctggtta atgccattgt cttcaaggac tgtgggagaa agcatttaag  1140
gatgaagaca cacaagcaat gcctttcaga gtgactgagc aagaaagcaa acctgtgcag  1200
atgatgtacc agattggttt atttagagtg gcatcaatgg ctctgagaaa atgaagatcc  1260
```

-continued

```
tggagcttcc atttgccagt gggacaatga gcatgttggt gctgttgcct gatgaagtct    1320
caggccttga gcagcttgag agtataatca actttgaaaa actgactgat ggaccagttc    1380
taatgttatg gaagagagga agatcaaagt gtacttacct cgcatgaaga tggaggaaaa    1440
atacaacctc acatctgtct taatggctat gggcattact gacgtgttta gctcttagcc    1500
aatctgtctg gcatctcctc agcagagagc ctgaagatat ctcaagctgt ccatgcagca    1560
catgcagaaa tcaatgaagc aggcagagag gtggtagggt cagcagaggc tggagtggat    1620
gctcaagcgt ctctgaagaa tttagggctg accatccatt cctcttctgt atcaagcaca    1680
tcgcaaccaa cgccgttctc ttctttggca gatgtgtttc ccct                     1724

<210> SEQ ID NO 14
<211> LENGTH: 576
<212> TYPE: PRT
<213> ORGANISM: Artificial
<220> FEATURE:
<223> OTHER INFORMATION: Fusion Protein

<400> SEQUENCE: 14

Met Asn Pro Ser Ser Asp Val Ala Ala Leu His Lys Ala Ile Met Val
1               5                   10                  15

Lys Gly Val Asp Glu Ala Thr Ile Ile Asp Ile Leu Thr Lys Arg Asn
                20                  25                  30

Asn Ala Gln Arg Gln Ile Lys Ala Ala Tyr Leu Gln Glu Thr Gly
            35                  40                  45

Lys Pro Leu Asp Glu Thr Leu Lys Lys Ala Leu Thr Gly His Leu Glu
        50                  55                  60

Glu Val Val Leu Ala Leu Leu Lys Thr Pro Ala Gln Phe Asp Ala Asp
65                  70                  75                  80

Glu Leu Arg Ala Ala Met Lys Gly Leu Gly Thr Asp Glu Asp Thr Leu
                85                  90                  95

Ile Glu Ile Leu Ala Ser Arg Thr Asn Lys Glu Ile Arg Asp Ile Asn
                100                 105                 110

Arg Val Tyr Arg Glu Glu Leu Lys Arg Asp Leu Ala Lys Asp Ile Ser
            115                 120                 125

Asp Thr Ser Gly Asp Phe Arg Asn Ala Leu Leu Ser Leu Ala Lys Gly
        130                 135                 140

Asp Arg Ser Glu Asp Phe Gly Val Asn Glu Asp Leu Ala Asp Ser Asp
145                 150                 155                 160

Ala Arg Ala Leu Tyr Glu Ala Gly Glu Arg Arg Lys Gly Thr Asp Val
                165                 170                 175

Asn Val Phe Asn Thr Ile Leu Thr Thr Arg Ser Tyr Pro Gln Leu Arg
                180                 185                 190

Arg Val Phe Gln Lys Tyr Thr Lys Tyr Ser Lys His Asp Met Asn Lys
            195                 200                 205

Val Leu Asp Leu Glu Leu Lys Gly Asp Ile Glu Lys Cys Leu Thr Ala
        210                 215                 220

Ile Val Lys Cys Ala Thr Ser Lys Pro Ala Phe Phe Ala Glu Lys Leu
225                 230                 235                 240

His Gln Ala Met Lys Gly Val Gly Thr Arg His Lys Ala Leu Arg Ile
                245                 250                 255

Met Val Ser Arg Ser Glu Ile Asp Met Asn Asp Ile Lys Ala Phe Tyr
                260                 265                 270

Gln Lys Met Tyr Gly Ile Ser Leu Cys Gln Ala Ile Leu Asp Glu Thr
            275                 280                 285
```

```
Lys Gly Asp Tyr Glu Lys Ile Leu Val Ala Leu Cys Gly Gly Asn His
290                 295                 300
Arg Gly Ser Gly Gly Ser Gly Gly Ser Glu Asn Leu Tyr Phe
305                 310                 315                 320
Gln Gly Gly Gly Ser Gly Gly Gly Ser Asp Gln Ala Arg Glu Leu
                325                 330                 335
Ile Asn Ser Trp Val Glu Ser Gln Thr Asn Gly Ile Ile Arg Asn Val
                340                 345                 350
Leu Gln Pro Ser Ser Val Asp Ser Gln Thr Ala Met Val Leu Val Asn
                355                 360                 365
Ala Ile Val Phe Lys Gly Leu Trp Glu Lys Ala Phe Lys Asp Glu Asp
370                 375                 380
Thr Gln Ala Met Pro Phe Arg Val Thr Glu Gln Glu Ser Lys Pro Val
385                 390                 395                 400
Gln Met Met Tyr Gln Ile Gly Leu Phe Arg Val Ala Ser Met Ala Ser
                405                 410                 415
Glu Lys Met Lys Ile Leu Glu Leu Pro Phe Ala Ser Gly Thr Met Ser
                420                 425                 430
Met Leu Val Leu Leu Pro Asp Glu Val Ser Gly Leu Glu Gln Leu Glu
                435                 440                 445
Ser Ile Ile Asn Phe Glu Lys Leu Thr Trp Thr Ser Ser Asn Val Met
                450                 455                 460
Glu Glu Arg Lys Ile Lys Val Tyr Leu Pro Arg Met Lys Met Glu Glu
465                 470                 475                 480
Lys Tyr Asn Leu Thr Ser Val Leu Met Ala Met Gly Ile Thr Asp Val
                485                 490                 495
Phe Ser Ser Ser Ala Asn Leu Ser Gly Ile Ser Ser Ala Glu Ser Leu
                500                 505                 510
Lys Ile Ser Gln Ala Val His Ala Ala His Ala Glu Ile Asn Glu Ala
                515                 520                 525
Gly Arg Glu Val Val Gly Ser Ala Glu Ala Gly Val Asp Ala Ala Ser
                530                 535                 540
Val Ser Glu Glu Phe Arg Ala Asp His Pro Phe Leu Phe Cys Ile Lys
545                 550                 555                 560
His Ile Ala Thr Asn Ala Val Leu Phe Phe Gly Arg Cys Val Ser Pro
                565                 570                 575

<210> SEQ ID NO 15
<211> LENGTH: 27
<212> TYPE: PRT
<213> ORGANISM: artificial
<220> FEATURE:
<223> OTHER INFORMATION: linker sequence

<400> SEQUENCE: 15

His Arg Gly Ser Gly Gly Ser Gly Gly Gly Ser Glu Asn Leu Tyr
1               5                   10                  15

Phe Gln Gly Gly Gly Gly Ser Gly Gly Gly Ser
                20                  25
```

CORE DOMAIN OF ANNEXINS AND USES THEREOF IN ANTIGEN DELIVERY AND VACCINATION

The present disclosure provides immunogenic compositions, such as vaccines, including DNA vaccines, and uses thereof, e.g., which include an annexin core domain for mediating efficient antigen delivery and antigen presentation in order to induce an antigen-specific immune response, and/or to treat or prevent infectious diseases and/or cancer.

BACKGROUND OF THE INVENTION

Central to the initiation of an adaptive immune response are professional antigen presenting cells (APC), which display antigen-derived peptides bound to MHC class I and class II complexes on their cell surface (Verboogen, Dingjan et al. 2016). While cytosolic proteins are degraded by the proteasome and loaded onto MHC class I complexes recognized by CD8+ T cells, engulfment of exogenous proteins (e.g. from phagocytosed bacteria or apoptotic cells) leads to endosomal/lysosomal degradation and presentation on MHC class II complexes presented to CD4+ T cells. In addition, APC such as dendritic cells (DC) are able to shuttle peptides derived from engulfed proteins also into the MHC class I pathway to be presented to CD8+ T cells, a process termed cross-presentation (Segura and Amigorena 2015). Amongst different cells types described to fulfill APC-like functions, DC are regarded as the most efficient (Kambayashi and Laufer 2014). Following APC:T cell interactions, T-cell receptors (TCR) engagement leads to initial T cell activation (priming), characterized, e.g., by secretion of cytokines like Interleukin (IL)-2 and Interferon-γ (Grakoui, Bromley et al. 1999). Activated T cells will proceed to divide and differentiate into different types of effector T cells, which can be classified in two major lineages, CD4+ T helper cells (Th) and CD8+ cytotoxic T cells. Cytotoxic T cells directly induce apoptosis in target cells, while Th cells direct immune responses by production of cytokines and have been classified into Th1, Th2 and Th17 major subsets (Lutz 2016). Summarizing their effector functions, Th1 cells are necessary to activate cellular immunity while Th2 cells induce humoral immune responses. Th17 cells are thought to be involved in immunity against extracellular pathogens like fungi. Regarding anti-tumor immune responses, the induction of efficient CD8+ T cell response has been regarded as critical for tumor rejection, and many tumor vaccination regimes fail to induce CD8+ T cell anti-tumor responses (Buhrman and Slansky 2013). Thus, efficient antigen presentation by APCs plays a pivotal role for induction of adaptive immunity.

Annexins comprise a family of calcium- and phospholipid-binding proteins. Over 20 members have been found in all eukaryotic kingdoms as well as plants and animals with the exception of fungi. Annexins have molecular weights ranging between 30 and 40 kDa (only annexin VI is 66 kDa) and possess striking structural features. Annexins' amino-terminal domains are diverse in sequence and length (ranging from 11 to 196) on each annexin member. In contrast the carboxyterminal regions consisting of four (eight only for annexin VI) a-helical domains composed of about 70 amino acid residues are well conserved among annexins. The calcium- and phospholipid-binding sites are located in the carboxyterminal domains. The $Ca^{2+}$ binding similarities of all the annexins is due to their common primary structure, a unique N-terminal domain (the "tail") and the conserved C-terminal domain (the "core"). With the exception of annexin VI, the conserved C-terminal domain is always composed of 4 repeats (annexin VI having 8) of ~70 amino acids containing an increased homology region called the "endonexin fold". In addition to the C terminal core the annexins contain a significantly more variable N terminal head. It is this domain which endows each annexin with unique functions in a diverse range of cellular processes including; endo- and exocytosis, cytoskeletal regulation and membrane conductance and organisation. Given their involvement in such a variety of processes it is not surprising that the annexins have also been implicated in a range of disease pathologies. Although there is no singular disease state directly attributed to a dysregulation in annexin function, several pathological conditions are suggested to be modified by the annexins. Fatimathas and Moss (Fatimathas and Moss 2010) discuss the growing evidence for the role of the annexins in the progression of cancer, diabetes and the autoimmune disorder anti-phospholipid syndrome.

In all annexins, lipid binding is mediated by the C-terminal core domain highly conserved among all annexin family members (Gerke and Moss 2002, Moss and Morgan 2004). In contrast, annexin N-termini vary in sequence. Peptides corresponding to the AnxA1 N-terminus were shown to bind to members of the N-formyl peptide receptor (FPR) family, resulting in a reduction of neutrophil transmigration in several models of acute and chronic inflammation (Walther, Riehemann et al. 2000, Strausbaugh and Rosen 2001, Ernst, Lange et al. 2004, Perretti and Dalli 2009). Downstream signaling induced by binding of AnxA1 N-terminal peptides to FPR family members causes activation of ERK, but not of p38 or JNK (Hayhoe, Kamal et al. 2006, Pupjalis, Goetsch et al. 2011). The presence of multiple annexin family members in all higher eukaryotes suggests a fundamental role for annexins in cell biology. Mice deficient in individual annexin family members, however, have no severe phenotype, suggesting that several annexins have (partly) overlapping functions (Gerke and Moss 2002, Farber, De Rose et al. 2003). In fact, functional redundancy of annexins was proven in the context of membrane trafficking, inhibition of PLA2 activity and blood coagulation (Gerke and Moss 2002).

US 2002-052358 describes a method of treating a subject with arthritis or an arthritic disease or preventing arthritis or arthritic disease in a subject, comprising administering to the subject a therapeutically effective amount of an agent that attenuates annexin function. Also provided are various methods of screening for agents.

WO 01/10199 describes a knockout transgenic mouse containing a nonfunctional allele of the tumor suppressing gene, annexin VII. This mouse is used as a screening model for potential therapeutic agents useful in the treatment of tumors resulting from an annexin tumor suppressor disease.

JP 2014-095643 describes screening of a compound effective in treatment of inflammatory disease, based on an inhibition of binding between annexin A2 and ADAM17.

WO 2014/126127 describes a method for screening an active ingredient for the treatment of severe enanthema, skin erythema, body surface erosion, blister and excoriation as formyl peptide receptor 1-induced necroptosis-related diseases. The active ingredient to be screened is said to be a substance capable of inhibiting necroptosis that is induced by the binding of formyl peptide receptor 1 to annexin A1.

WO 02/17857 discloses methods for inhibiting angiogenesis in endothelial cells and selectively inducing apoptosis in endothelial cells via compounds which binds annexin II are provided. These compounds and methods for using these compounds are regarded as useful in the treatment of diseases or disorders characterized by unwanted angiogenesis. Also provided are pharmaceutical compositions containing a compound which binds annexin II and a pharmaceutically acceptable vehicle and methods for identifying such compounds.

WO 2005/027965 discloses anti-annexin antibodies and their uses as well as uses of theirs ligands, the annexins. Such annexins and anti-annexin antibodies are useful for detecting apoptosis and for the production of pharmaceutical compositions for the diagnosis and/or treatment of cancer, autoimmune diseases, cardiovascular and/or vascular diseases.

US 2014/0322214 discloses includes compositions and methods for binding Dectin-1 on immune cells with anti-Dectin-1-specific antibodies or fragment thereof capable of activating the immune cells as well as methods for treating or preventing an influenza infection in a subject in need thereof comprising administering to the subject a therapeutically effective amount of a composition comprising an anti-dectin-1 antibody fused to an influenza antigen. The thesis of Connie Hesse, CLEC7A/Dectin-1 attenuates the immune response against dying and dead cells, Friedrich-Alexander-University Erlangen-Nürnberg, 2011, discusses the role of C-type lectins CLEC4L/DC-SIGN, CLEC9A/DNGR1, and CLEC7A/dectin-1 in the recognition as well as the uptake of apoptotic and necrotic cells and/or their effects on the immunogenicity of dying and dead cells.

The low-density lipoprotein receptor-related protein-1 (LRP-1) is a membrane receptor displaying both scavenging and signaling functions. The wide variety of extracellular ligands and of cytoplasmic scaffolding and signaling proteins interacting with LRP-1 gives it a major role not only in physiological processes, such as embryogenesis and development, but also in critical pathological situations, including cancer and neurological disorders (Emonard, Theret et al. 2014). Cell surface annexin VI may function as an acidic pH binding site or receptor and may also function as a co-receptor with LRP-1 at neutral pH in the context of alpha 2-macroglobulin recognition (Ling, Chen et al. 2004).

Arur and colleagues (Arur, Uche et al. 2003) as well as Tzelepis et al. (Tzelepis, Verway et al. 2015) describe a role for annexin A1 in the process of phagocytosis of apoptotic cells, which is regarded as immunologically silent and not leading to a T cell response. In the same publication, Tzelepis and colleagues further described a role for endogenous annexin A1 in the process of cross presentation. This publication describes annexin A1 as a mediator that acts in the cytosol of dendritic cells. Therefore, this publication does not enable the use of the annexin core domain as exogenous mediator to engage antigen presentation and cross presentation.

Andersen and colleagues (Andersen, Xia et al. 2016) describe the binding of annexin A2 to Toll-like receptor (TLR) 2. By triggering TLR2, annexin A2 can act as a vaccine adjuvant, enhancing TLR-mediated DC activation and processes like upregulation of co-stimulatory surface molecules and antigen cross-presentation. This publication is silent about antigen delivery into DC.

Tzelepis et al. (in: Tzelepis et al. Annexin1 regulates DC efferocytosis and cross-presentation during *Mycobacterium tuberculosis* infection. J Clin Invest. 2015 February; 125(2): 752-68. Epub 2014 Dec. 22) disclose that during *Mycobacterium tuberculosis* (Mtb) infection, the engulfment ligand annexin1 is an important mediator in DC cross-presentation that increases efferocytosis in DCs and intrinsically enhances the capacity of the DC antigen-presenting machinery. Annexin1-deficient mice were highly susceptible to Mtb infection and showed an impaired Mtb antigen-specific CD8+ T cell response.

Finally, Weyd and colleagues (Weyd, Abeler-Dorner et al. 2013, Linke, Abeler-Dorner et al. 2015) disclose that in mice, Annexin A1, Annexin A5, Annexin A13 and the annexin core domain prevented the development of inflammatory DC and suppressed the cellular immune response against the model antigen ovalbumin (OVA) expressed in apoptotic cells.

Reagents which react specifically or preferentially with DC and mediate antigen presentation have great potential as targeting agents to induce potent immune responses to tumor or infectious disease antigens. These cell-specific targeting agents could also be engineered to deliver toxins to eliminate potent antigen presenting cells (e.g., DC) in bone marrow and organ transplantations or other autoimmune disorders. Accordingly, such DC-specific binding agents possess great therapeutic and diagnostic value.

It is therefore an object of the present invention to provide such new reagents and to employ these reagents in the development of new and effective therapies. Other objects and aspects of the present invention will become apparent to the person of skill upon reading the following description of the invention.

The invention pertains to an isolated annexin core domain, the annexin core domain being defined to comprise an amino acid sequence of an annexin core domain shown within the sequence selected from the group of SEQ ID Nos. 1 to 3 and 6 to 8, or to comprise an amino acid sequence that is at least 50%, 60%, 70%, 80%, 85%, 90%, 95%, 98%, most preferably 99% identical to an annexin core domain amino acid sequence as comprised within a sequence selected from the group of SEQ ID Nos. 1 to 3 and 6 to 8. The definitions of the core domains is provided herein below in the example section. In particular preferred is an annexin core domain consisting of an amino acid sequence of a core domain as shown in an amino acid sequence selected from the group of SEQ ID Nos. 1 to 3 and 6 to 8; or consisting of an amino acid sequence that is at least 50%, 60%, 70%, 80%, 85%, 90%, 95%, 98%, most preferably 99% identical to an amino acid sequence of a core domain as shown in an amino acid sequence selected from the group of SEQ ID Nos. 1 to 3 and 6 to 8.

The present invention also provides a protein conjugate or fusion protein comprising (i) at least one annexin core domain as described herein, and (ii) at least one antigenic peptide that can be presented by MHC (preferably HLA). The antigenic peptide can be derived from a tumor or infectious agent, pathogen or endogenous protein. The present invention also provides respective vaccines comprising fusions and/or conjugates and other therapeutic compositions.

In certain embodiments the protein conjugate or fusion protein of the invention comprises a covalent linkage between the annexin core domain and the at least one antigenic peptide that can be presented by MHC. Also encompassed are conjugates or fusion protein of the invention where the covalent linkage includes a linker molecule or peptide. Selection of suitable linker molecules is well established in the pertinent art. In some embodiments of the invention the linker comprises an amino acid sequence of the linker as shown in FIG. 10A (SEQ ID NO: 15), or a sequence having at least 80%, 85%, 90%, 95%, 96%, 97%, 98% or 99% sequence identity to the linker sequence shown in FIG. 10B (SEQ ID NO: 15).

In some aspects and embodiments the present invention the fusion protein is encoded by the nucleic acid shown in SEQ ID NO: 13, or a by a nucleic acid variant thereof having at least 80%, 85%, 90%, 95%, 96%, 97%, 98% or 99% sequence identity to SEQ ID NO: 13. Preferably the fusion protein of the invention comprises the amino acid sequence of SEQ ID NO: 14, or of a variant thereof having at least 80%, 85%, 90%, 95%, 96%, 97%, 98% or 99% sequence identity to SEQ ID NO: 14.

The term "fusion protein" as used herein relates to an artificial proteinaceous construct and means a protein comprising at least two different amino acid sequences which are defined by their origin and/or by special functions. In this aspect the fusion protein of the invention comprises the annexin core domain amino acid sequence fused to second amino acid sequence of another protein which is not annexin, and which is antigenic in the sense that said second protein or fragments thereof, are presented on a cell via the MHC complex. Moreover, the term fusion protein according to the present invention does further include such fusion proteins which also contain non-protein molecules such as nucleic acids, sugars, or markers for radioactive or fluorescent labelling.

It was surprisingly found that the constructs according to the present invention have an immune stimulating (enhancing) effect. Thus, the compositions of the invention containing the annexin core domain complex and/or fusion can be used in a variety of DC-targeted therapies, for example, to enhance antigen presentation and/or induce T cell responses, such as cytotoxic T cell (CTL) responses, against a variety of target cells or pathogens, or to treat antigen presenting cell (APC)-mediated diseases. The invention surprisingly found that combining an antigenic molecule, such as an antigenic peptide, with an annexin core domain as described herein, significantly enhances the immune modulatory effects of said antigenic sequence. Without being bound to a particular theory, coupling an annexin core domain to an antigenic molecule enhances antigen processing and MHC-presentation of antigen presenting cells such as dendritic cells. Therefore the invention broadly enables a products and methods for enhancing the antigen presentation of antigenic molecules via MHC, preferably human MHC (HLA).

As used herein, the term "antigen" refers to a substance capable of eliciting an immune response, e.g., a T-cell-mediated immune response by the presentation of the antigen on Major Histocompatibility Antigen (MHC) cellular proteins and causing an antigen-specific T-cells response. In the case of a regulatory T-cell (Treg) response to the antigen is a decrease or amelioration of the immune response by other effector cells, e.g., helper T-cells (Th) and/or cytotoxic T-cells (Tc). The skilled immunologist will recognize that when discussing antigens that are processed for presentation to T-cells, the term "antigen" refers to those portions of the antigen (e.g., a peptide fragment) that is a T-cell epitope presented by MHC to the T-cell receptor. When the expression "antigen" is modified by self- or auto-, this refers to self or auto antigens that are commonly present in MHC molecules but that also trigger a T-cell response. When used in the context of a B cell mediated immune response in the form of an antibody that is specific for an "antigen", the portion of the antigen that binds to the complementarity determining regions of the variable domains of the antibody (light and heavy) the bound portion may be a linear or three-dimensional epitope. In certain cases, the antigens delivered by the vaccine or fusion protein or protein conjugate of the present invention are internalized and processed by antigen presenting cells prior to presentation, e.g., by cleavage of one or more portions of the antibody or fusion protein.

As used herein, the term "antigenic peptide" refers to that portion of a polypeptide antigen that is specifically recognized by either B-cells and/or T-cells. B-cells respond to foreign antigenic determinants via antibody production, whereas T-lymphocytes mediate cellular immunity. Thus, antigenic peptides in a T-cell response are those parts of an antigen that are recognized by antigen-specific T-cell receptors in the context of MHC.

As used herein, the term "epitope" refers to any protein determinant capable of specific binding to an immunoglobulin or of being presented by a Major Histocompatibility Complex (MHC) protein (e.g., Class I or Class II) to a T-cell receptor. Epitopic determinants are generally short peptides 5-30 amino acids long that fit within the groove of the MHC molecule that presents certain amino acid side groups toward the T-cell receptor and has certain other residues in the groove, e.g., due to specific charge characteristics of the groove, the peptide side groups and the T-cell receptor. Generally, an antibody specifically binds to an antigen when the dissociation constant is 1 mM, 100 nM or even 10 nM.

As used herein the term "Antigen Presenting Cells" (APC) are cells that are capable of activating T-cells, and include, but are not limited to, certain macrophages, B cells and dendritic cells. "Dendritic cells" (DCs) refer to any member of a diverse population of morphologically similar cell types found in lymphoid or non-lymphoid tissues. These cells are characterized by their distinctive morphology, high levels of surface MHC-class II expression (Steinman, et al., Ann. Rev. Immunol. 9:271 (1991); incorporated herein by reference for its description of such cells). These cells can be isolated from a number of tissue sources, and conveniently, from peripheral blood or differentiated from murine bone marrow, as described herein. Dendritic cell binding proteins refer to any protein for which receptors are expressed on a dendritic cell. Examples include GM-CSF, IL-1, TNF, IL-4, CD40L, CTLA4, CD28, and FLT-3 ligand. An antigenic peptide comprises a peptide sequence that is capable to be presented by HLA molecules (MHC class I and/or MHC class II) and induces a T cell response, such as cytotoxic T cell (CTL) response. Usually, these peptides are between 8 and 30, preferably between 8 and 24 amino acids long, MHC class I peptides are usually between 8 and 10 long, and MHC class II peptides are usually between 21 and 25 amino acids long. Methods to identify ("screen") for these antigenic peptides are known as well and can involve both in vivo or in vitro and in silico methods.

Methods to prepare respective conjugates (i.e. comprising non-covalent or covalent bonds introduced between different components, i.e. the annexin and the peptide) of the annexin core domain and the antigenic peptide as well as to prepare respective fusion proteins (i.e. expression of one protein after recombinant cloning of the components) are well known in the art.

In the context of the present invention, the term "annexin core domain" shall be understood as indicating/representing the minimal fragment of the polypeptide for annexin (or homologs thereof), which is necessary and sufficient to mediate antigen presentation (see also below). Some preferred proteinaceous annexin core domains are defined herein above. This ability (biological function) may be tested in a number of art known methods as described herein, and, e.g. in the examples, below. This ability may further be tested in a number of art known methods as described in the respective literature. For examples of annexin core domains, see also FIG. 7, below. Also, the term shall particularly comprise the vertebrate, in particular mammalian (in particular human) annexin gene and/or protein and/or mRNA and/or the core fragment (core domain) as described herein. The term also covers the annexin core domain in different preparations, such as in the cellular context, a cell recombinantly expressing said core domain, purified from the cell, and fractions, in particular biologically active factions, thereof.

Protein aggregates are known to enhance immune responses. The mechanism by which protein aggregates mediate such potent antibody responses is not fully understood. However, it is believed that the potency is due, at least in part, to the ability of the multivalent protein to extensively cross link the cell surface receptors such as immunoglobulins of B cells and activate the B cells. Therefore it is in context of the invention one embodiment to aggregate the protein conjugate or fusion protein of the invention to further enhance immune responses. This may be achieved by using multimeric antigenic peptides where the antigenic molecule is multimerized directly or via a linker sequence to form a poly-antigenic peptide with a repeating antigenic sequence for fusion with the annexin core domain in accordance with the invention. Alternatively the fusion protein of the invention may further comprise a moiety that induces aggregation of the protein conjugate or fusion protein, such as a protein multimerization domain or dimerization domain, which is covalently attached to the fusion protein. One particularly favorable example of such a protein multimerization domain is a coiled-coil domain, such as an isoleucine zipper domain that promotes trimerization of multiple polypeptides having such a domain. A further favorable example of a modification for protein multimerization is the use of conjugated biotin or a biotinylation sequence in conjunction with the protein streptavidin. Another option in context of the invention provides compositions of the fusion protein of the invention in combination with the agent for protein aggregation.

Fusion proteins can also be made at the nucleic acid coding level by placing, in-line and in the correct coding frame, the two or more sequences of the portions of the proteins or peptides, i.e. of the annexin core domain and the respective antigenic peptide or antigen. Fusion proteins are synthesized by methods known to those of skill in the art including, e.g., solid phase protein synthesis, and by molecular techniques that permit the manipulation of DNA in vitro, including polymerase chain reaction (PCR) and oligonucleotide-directed mutagenesis.

In the context of the present invention, the terms "C-type lectin receptor", "Dectin-1", "DC-SIGN", and "LRP-1" shall be understood as indicating/representing the minimal fragment of the receptor(s), which is necessary and sufficient to bind to a core domain of the annexin as described and tested in the examples, and in, for example, Hesse as mentioned above for lectin-Fc fusion proteins. This ability may further be tested in a number of art known methods as described in the respective literature. Also, the term shall comprise the mammalian (in particular mouse) homolog of the human receptor gene and/or protein and/or mRNA and/or the fragment (binding part, fragment or domain) as described herein. The term also covers the receptor(s) and/or the minimal fragment of the receptor(s) in different preparations, such as in the cellular context, a cell (recombinantly) expressing said receptor(s) and/or the minimal fragment of the receptor(s), purified from the cell, and fractions thereof.

With Dectin-1 and DC-SIGN as members of the family of C-type lectin receptors and LRP-1, novel DC-surface receptors could be identified that with high affinity bind to the core domain of all annexins as studied. This is an indication that Dectin-1, DC-SIGN and LRP-1 are responsible for the annexin-mediated effects on the immune response and induction of antigen presentation.

The effect of the annexins on DC via specific receptors is a novel molecular mechanism of antigen presentation, resulting in a multitude of novel possibilities both for the therapy of cancers and tumors, as well as for infectious diseases in mammals, such as mice and humans.

WO 2009/049892 describes a first polypeptide (A) comprising a recruiting polypeptide (a) comprising at least an annexin core domain or a functional variant thereof, a bait polypeptide (b) and a luminophore. The composition according to the invention can be used to measure protein-protein interactions within and/or between entire multiprotein complexes. Described is the use of the method according to the invention for the identification of a test compound in a library of test compounds which modulates a medically relevant protein-protein interaction, without that any concrete disease context is disclosed. WO 2009/049892 is silent about any interaction(s) of annexin with Dectin-1, DC-SIGN and/or LRP-1, and also non-enabling for the screening of therapeutically relevant compounds and/or compositions.

WO 2005/027965 describes that annexin I and other annexins are related to specific receptors, which could be stimulated or blocked by either binding of one of the annexins or fragments thereof or an antibody against this receptor. Thus, annexins and/or functional fragments thereof and/or fusion proteins comprising an annexin or functional fragments thereof are discussed to be of use to modulate the immune system. WO 2005/027965 is silent about the use of the annexin core domain itself to mediate antigen presentation, and thus is also non-enabling for the screening of therapeutically relevant compounds and/or compositions.

Exposure of bone marrow-derived DC (BMDC) to a fusion protein comprising the annexin core domain and the model antigen ovalbumin (OVA) in vitro resulted in profound antigen presentation of OVA-derived peptides in surface MHC class I molecules (FIG. 1) as well as in strongly amplified specific T cell stimulation of both, CD8+ and CD4+ T cells (FIGS. 2 and 3). These results suggest that the annexin core domain has a previously unappreciated role in antigen presentation and antigen cross-presentation. Manipulating anx-core-domain mediated antigen presentation may, therefore, prove useful when designing vaccination strategies and, accordingly, beneficial for patients with cancer (vaccination with tumor antigens) or infectious diseases. Of note, this mechanism, in which the annexin core domain mediates antigen delivery and antigen presentation when administered exogenously to DC and linked to an antigen is inherently different from described endogenous, cytosolic functions of annexin A1 (Tzelepis, Verway et al. 2015). This mechanism is also different from described vaccine adjuvant function of annexin A2 binding to Toll-like receptor 2 (Andersen, Xia et al. 2016), because the annexin core domain as described here does not mediate DC stimulation via TLRs but mediates antigen delivery and antigen (cross-) presentation.

Preferred is a protein conjugate or fusion protein according to the present invention, wherein said antigenic peptide is derived from a protein selected from the group consisting of βhCG, gp100 or Pmel17, HER2/neu, WT1, mesothelin, CEA, gp100, MART1, TRP-2, NY-BR-1, NY-CO-58, MN (gp250), idiotype, Tyrosinase, Telomerase, SSX2, MUC-1, MART1, melan-A, NY-ESO-1, MAGE-1, MAGE-3, MAGE-A3, and high molecular weight-melanoma associated antigen (HMW-MAA).

Other antigenic peptides for use with the present invention include cancer peptides selected from tumor-associated antigens, e.g., autologous cancer antigens obtained from a patient. Non-limiting examples of cancer antigens include antigens from leukemias and lymphomas; neurological tumors such as astrocytomas or glioblastomas; melanoma; breast cancer; lung cancer; head and neck cancer; gastrointestinal tumors; gastric cancer; colon cancer; liver cancer; pancreatic cancer; genitourinary tumors such cervix; uterus; ovarian cancer; vaginal cancer; testicular cancer; prostate cancer or penile cancer; bone tumors; vascular tumors; or cancers of the lip; nasopharynx; pharynx and oral cavity; esophagus; rectum; gall bladder; biliary tree; larynx; lung and bronchus; bladder; kidney; brain and other parts of the nervous system; thyroid; Hodgkin's disease; non-Hodgkin's lymphoma; multiple myeloma and leukemia. In a specific aspect the composition further comprises antigenic peptides selected from tumor associated antigens are selected from CEA; prostate specific antigen (PSA); HER-2/neu; BAGE; GAGE; MAGE 1-4; 6 and 12; MUC (Mucin) (e.g.; MUC-1, MUC-2, etc.); GM2 and GD2 gangliosides; ras; myc; tyrosinase; MART (melanoma antigen); MARCO-MART; cyclin Bl; cyclin D; Pmel 17(gp100); GnT-V intron V sequence (N-acetylglucoaminyltransferase V intron V sequence); Prostate Ca psm; prostate serum antigen (PSA); PRAME (melanoma antigen); β-catenin; MUM-1-B (melanoma ubiquitous mutated gene product); GAGE (melanoma antigen) 1; BAGE (melanoma antigen) 2-10; C-ERB2 (Her2/neu); EBNA (Epstein-Barr Virus nuclear antigen) 1-6; gp75; human papilloma virus (HPV) E6 and E7; p53; lung resistance protein (LRP); Bcl-2; and Ki-67.

Further antigenic peptides or antigens for use in context with the present invention are selected from viral antigens. The term "viral antigen" includes any substance that elicits an immune response against a virus. Examples include Retro viridae, in particular HIV-I and HIV-LP; Picornaviridae, in particular polio virus and hepatitis A virus; enterovirus, in particular human coxsackie virus, rhinovirus, echovirus; Calciviridae, in particular strains that cause gastroenteritis; Togaviridae, in particular equine encephalitis virus and rubella virus; Flaviridae, in particular dengue virus, encephalitis virus and yellow fever virus; Coronaviridae, in particular coronavirus; Rhabdoviridae, in particular vesicular stomatitis virus and rabies virus; Filoviridae, in particular Ebola virus or and Marburg virus; Paramyxoviridae, in particular parainfluenza virus, mumps virus, measles virus and respiratory syncytical virus; Orthomyxoviridae, in particular influenza virus; Bungaviridae, in particular Hantaan virus, bunga virus, phlebovirus and Nairo virus; Arena viridae, in particular hemorrhagic fever virus; Reoviridae, in particular reovirus, orbivirus and rotavirus; Birnaviridae; Hepadnaviridae, in particular Hepatitis B virus; Parvovirida, in particular parvovirus; Papovaviridae, in particular papilloma virus, simian virus-40 (SV40) and polyoma virus; Adenoviridae; Herpesviridae, in particular herpes simplex virus (HSV) 1 and 2, varicella zoster virus, cytomegalovirus (CMV), herpes virus; Poxyiridae, in particular variola virus, vaccinia virus and pox virus; and Irido viridae, in particular African swine fever virus; Hepatitis C, and HPV L6, HPV L7, fragments and derivatives thereof.

Further antigenic peptides or antigens for use in context with the present invention are selected from bacterial antigens. As used herein, the term "bacterial antigen" includes any substance that elicits an immune response against a bacterium. Examples include *Helicobacter* species, in particular *Helicobacter pyloris*; *Borrelia* species, in particular *Borrelia burgdorferi*; *Legionella* species, in particular *Legionella pneumophilia*; *Mycobacteria* species, in particular *M. tuberculosis, M. avium, M. intracellulare, M. kansasii, M. gordonae*; *Staphylococcus* species, in particular *Staphylococcus aureus*; *Neisseria* species, in particular *N. gonorrhoeae, N. meningitidis*; *Listeria* species, in particular *Listeria monocytogenes*; *Streptococcus* species, in particular *S. pyogenes, S. agalactiae; S. faecalis; S. bovis, S. pneumoniae*; anaerobic *Streptococcus* species; pathogenic *Campylobacter* species; *Enterococcus* species; *Haemophilus* species, in particular *Haemophilus influenzae*; *Bacillus* species, in particular *Bacillus anthracia*; *Corynebacterium* species, in particular *Corynebacterium diphtheriae*; *Erysipelothrix* species, in particular *Erysipelothrix rhusiopathiae*; *Clostridium* species, in particular *C. perfringens, C. tetani*; *Enterobacter* species, in particular *Enterobacter aerogenes*, *Klebsiella* species, in particular *Klebsiella pneumoniae*, *Pasteurella* species, in particular *Pasteurella multocida*, *Bacteroides* species; *Fusobacterium* species, in particular *Fusobacterium nucleatum; Streptobacillus* species, in particular *Streptobacillus moniliformis; Treponema* species, in particular *Treponema pertenue; Leptospira*; pathogenic *Escherichia* species; and *Actinomyces* species, in particular *Actinomyces israelii*.

Preferred is furthermore a protein conjugate or fusion protein according to the present invention, wherein said conjugate or said fusion protein is further conjugated/fused to a co-stimulatory molecule or an immunogenic fragment thereof or a costimulatory second peptide sequence.

Another aspect of the present invention then relates to a nucleic acid encoding for the fusion protein or protein conjugate according to the present invention. Preferably, the coding sequence codes for an antigen derived from a protein selected from the group consisting of βhCG, gp100 or Pmel17, HER2/neu, WT1, mesothelin, CEA, gp100, MART1, TRP-2, NY-BR-1, NY-CO-58, MN (gp250), idiotype, Tyrosinase, Telomerase, SSX2, MUC-1, MART1, melan-A, NY-ESO-1, MAGE-1, MAGE-3, MAGE-A3, and high molecular weight-melanoma associated antigen (HMW-MAA). More preferably, said coding sequence is fused to at least one (additional) DC-stimulatory nucleic acid sequence. It is also possible to use fusions of multiple antigenic peptides, for example multiple sequences found in one tumor disease, or patient specific antigens found in an individual tumor.

Another aspect of the present invention then relates to a recombinant expression vector expressing the nucleic acid according to the invention.

The invention also relates to an isolated annexin core domain comprising an amino acid sequence of the core domain as shown in the sequences selected from SEQ ID Nos. 1 to 3 and 6 to 8. The domain ranges are provided herein in the example section. Preferred are domains consisting of said sequences, or essentially consist of said sequences (e.g. having 5 to 10 amino acid extensions that do not interfere with the function of the domain). The annexin core domain according to the present invention that can further be used in the method according to the present invention can be derived from any of the known annexins or functional fragments (i.e. able to bind to the receptors as described herein) thereof, and is preferably selected from the group of the human or murine annexin 1, 5, and 13 core domain, preferably according to a sequence comprised in the sequence according to SEQ ID NO: 1 to 3 and 6 to 8, or according to a sequence of a core comprised in the sequence according to SEQ ID NO: 1,2,3,6,7, or 8, or functional fragments thereof, more preferably according to the boxed sequences as shown in FIG. 8.

The term "contact" in the present invention means any interaction between the potentially binding substance(s)/antigens with the annexin core domain, whereby any of the two components can be independently of each other in a liquid phase, for example in solution, or in suspension or can be bound to a solid phase, for example, in the form of an essentially planar surface or in the form of particles, pearls or the like.

Another aspect of the present invention relates to a method for manufacturing a pharmaceutical composition for treating or preventing infectious diseases or cancer, comprising the step of admixing the protein conjugate or fusion protein according to the present invention, or the nucleic acid according to the present invention, or the expression vector according to the present invention, with a suitable agent or carrier.

Thus, the compounds of the invention can be admixed with suitable auxiliary substances and/or additives. Such substances comprise pharmacological acceptable substances, which increase the stability, solubility, biocompatibility, or biological half-life of the interacting compound or comprise substances or materials, which have to be included for certain routs of application like, for example, intravenous solution, sprays, band-aids or pills.

Carriers, excipients and strategies to formulate a pharmaceutical composition, for example to be administered systemically or topically, by any conventional route, in particular enterally, e.g. orally, e.g. in the form of tablets or capsules, parenterally, e.g. in the form of injectable solutions or suspensions, topically, e.g. in the form of lotions, gels, ointments or creams, or in nasal or a suppository form are well known to the person of skill and described in the respective literature.

Another aspect of the present invention thus is a pharmaceutical composition comprising the protein conjugate or fusion protein according to the present invention, or the nucleic acid according to the present invention, or the expression vector according to the present invention. Preferably, the pharmaceutical composition is a vaccine.

Administration of an agent, e.g., the complex or fusion, can be accomplished by any method which allows the agent to reach the target cells. These methods include, e.g., injection, deposition, implantation, suppositories, oral ingestion, inhalation, topical administration, or any other method of administration where access to the target cells by the agent is obtained. Injections can be, e.g., intravenous, intradermal, subcutaneous, intramuscular or intraperitoneal. Implantation includes inserting implantable drug delivery systems, e.g., microspheres, coated microparticles, hydrogels, polymeric reservoirs, cholesterol matrices, polymeric systems, e.g., matrix erosion and/or diffusion systems and non-polymeric systems, e.g., compressed, fused or partially fused pellets. Suppositories include glycerin suppositories. Oral ingestion doses can be enterically coated. Inhalation includes administering the agent with an aerosol in an inhalator, either alone or attached to a carrier that can be absorbed. The agent can be suspended in liquid, e.g., in dissolved or colloidal form. The liquid can be a solvent, partial solvent or non-solvent. In many cases, water or an organic liquid can be used.

In certain embodiments, the compound (activator or inhibitor) is administered to the subject by administering a recombinant nucleic acid, such as, for example, an annexin core domain or antigen RNA. Preferably, the recombinant nucleic acid is a gene therapy vector.

Another aspect of the present invention relates to a method or use as described herein, wherein the pharmaceutical composition further comprises additional pharmaceutically active ingredients for treating or preventing autoimmune diseases, chronic inflammatory diseases, allergies or cancer, i.e. chemotherapeutics.

Another aspect of the present invention relates to an isolated annexin core domain; a complex or fusion of an annexin core domain with at least one antigen; an activating antibody, optionally coupled to at least one antigen or allergenic compound; or a pharmaceutical composition according to the present invention for use in the prevention and/or therapy of diseases as described herein (see, e.g., below). Preferred is the complex or fusion for use according to the present invention, wherein said complex or fusion is soluble or bound to a carrier, such as a liposome or latex bead.

Another aspect of the present invention then relates to a method for treating or preventing infectious diseases or cancer in a patient, comprising administering to said patient an effective amount of an isolated annexin core domain; a complex or fusion of an annexin core domain with at least one antigen or allergenic compound; an activating antibody, optionally coupled to at least one antigen or allergenic compound; or a pharmaceutical composition obtained by the method according to the present invention.

In general, the attending physician will base a treatment on the compound as identified, and optionally also on other individual patient data (clinical data, family history, DNA, etc.), and a treatment can also be performed based on the combination of these factors. This method of the present invention for example involves integrating individual diagnostic immunological data with patient clinical information and general healthcare statistics to enable, for example, the application of personalized medicine to the patient. Significant information about drug effectiveness, drug interactions, and other patient status conditions can be used, too.

Preferred is a therapeutic method according to the present invention, wherein said mammal to be treated is a mouse, rat or human.

Preferably, an active agent of the invention (preferably the annexin core domain or the protein conjugate or fusion protein of the invention) is administered in form of a pharmaceutical composition comprising an activating agent as described above, such as an antibody, nucleotide or an activating binding compound for the annexin core domain/receptor binding. Preferably, said patient is a human being. Treating is meant to include, e.g., preventing, treating, reducing the symptoms of, or curing the disease or condition, i.e. immunological diseases such as immunodeficiency, infectious diseases or cancer.

In general, the attending physician will base a treatment on the compound as identified, and optionally also on other individual patient data (clinical data, family history, DNA, etc.), and a treatment can also be performed based on the combination of these factors. This method of the present invention for example involves integrating individual diagnostic cancer data with patient clinical information and general healthcare statistics to enable, for example, the application of personalized medicine to the patient. Significant information about drug effectiveness, drug interactions, and other patient status conditions can be used, too.

Preferred is a therapeutic method according to the present invention, wherein said mammal to be treated is a mouse, rat or human.

More preferably, the cancer to be treated is a solid tumor, such as, for example, selected from breast, bone, ovarian, liver, kidney, and lung cancer.

Preferably, an active agent is administered in form of a pharmaceutical composition, such as a protein conjugate or fusion protein of the invention, said patient is a human being. Treating is meant to include, e.g., preventing, treating, reducing the symptoms of, or curing the disease or condition, i.e. cancer. Treatment generally involves the administration of a therapeutically effective amount of the protein conjugate or fusion protein of the invention to the subject in need of the treatment.

In another aspect the invention provides a method for the vaccination of a subject comprising the administration of the protein conjugate or fusion protein of the invention to the subject in need of vaccination. The protein conjugate or fusion protein of the invention is preferably in the form of a vaccine composition and comprises additionally at least one carrier and/or excipient and/or vaccine adjuvant.

The herein disclosed pharmaceutical and in particular vaccine compositions preferably further comprise one or more immune stimulatory compounds such as adjuvants. An "adjuvant" is an agent that enhances the production of an immune response in a non-specific manner. Common adjuvants include suspensions of minerals (alum, aluminum hydroxide, aluminum phosphate) onto which the fusion protein of the invention is adsorbed; emulsions, including water-in-oil, and oil-in-water (and variants thereof, including double emulsions and reversible emulsions), liposaccharides, lipopolysaccharides, immunostimulatory nucleic acids (such as CpG oligonucleotides), liposomes, Toll-like Receptor agonists (particularly, TLR2, TLR4, TLR7/8 and TLR9 agonists), and various combinations of such components.

An "effective amount" is an amount of the compound(s) or the pharmaceutical composition as described herein that increases antigen presentation. The amount alleviates symptoms as found for the disease and/or condition.

The invention also includes a method for treating a subject at risk for infectious diseases or cancer, wherein a therapeutically effective amount of an annexin core domain conjugate is provided. Being at risk for the disease can result from, e.g., a family history of the disease, a genotype which predisposes to the disease, or phenotypic symptoms which predispose to the disease.

The mammalian patient can be a rat, mouse, goat, rabbit, sheep, horse, monkey or human, preferred is a mouse, rat or human.

Yet another preferred aspect of the present invention then relates to a kit, comprising materials for vaccination according to the present invention as described herein, in one or separate containers, preferably comprising a screening tool according to the present invention. Optionally, the kit comprises instructions for performing a method according to the present invention as described herein.

The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The container may be formed from a variety of materials such as glass or plastic. Preferably the kit and/or container contain/s instructions on or associated with the container that indicates directions for reconstitution and/or use.

Preferred is a kit according to the present invention, wherein said kit comprises materials for a method selected from the group of Western blots and/or Enzyme-Linked Immunosorbent Assay (ELISA). For example, the label may indicate that the lyophilized formulation is to be reconstituted to certain antibody concentrations as suitable for the above methods, such as ELISA.

Further preferred is the use according to the present invention, wherein said kit comprises monoclonal antibodies or fragments thereof specific for the annexin core domain and/or functional parts and variants thereof as described herein.

The following figures, sequences, and examples merely serve to illustrate the invention and should not be construed to restrict the scope of the invention to the particular embodiments of the invention described in the examples. All references as cited herein are hereby incorporated in their entirety by reference.

FIG. 1 shows that a fusion protein containing the annexin core domain and the model antigen ovalbumin (Anx-OVA) leads to strongly enhanced antigen cross-presentation in MHC class I molecules on dendritic cells (DC) compared to the antigen OVA alone. A) Schematic presentation of the experiment. Murine bone marrow derived DC were incubated with OVA or Anx-OVA. Cross presented OVA-derived peptide SIINFEKL (SEQ ID NO: 4) within MHC I molecules on DC was detected by a specific antibody (anti-MHC-SIINFEKL (SEQ ID NO: 4), antibody 25-D1.16, eBioscience). B) Representation of DC positive for cross presented OVAderived peptide SIINFEKL (SEQ ID NO: 4), as detected in flow cytometry after incubation with equal amounts (500 nM) of OVA or Anx-OVA for 12 h. N=3

FIG. 2 shows that incubation of DC with a fusion protein containing the annexin core domain and the model antigen ovalbumin (Anx-OVA) leads to strongly enhanced CD8+ T cell activation compared to incubation with the antigen OVA alone. A) Schematic presentation of the experiment. Murine bone marrow derived DC were incubated with OVA or Anx-OVA. CD8+ T cell activation was detected using CD8+ OT-I T cells that carry a transgenic T cell receptor specific for the OVA-derived SIINFEKL (SEQ ID NO: 4) peptide. T cell activation was detected by secretion of Interferon-© (IFN-©). B) Murine bone marrow derived DC were incubated with equal amounts of OVA or Anx-OVA, or with purified SIINFEKL (SEQ ID NO: 4)-peptide as positive control. After 12 h of incubation, DC were co-cultured for further 3-5 days with OT-IT cells. OT-I T cell activation was detected by measuring IFN-© secretion in ELISA. N=3

FIG. 3 shows that incubation of DC (OVA-derived peptide SIINFEKL (SEQ ID NO: 4) within MHC I molecules on DC) with a fusion protein containing the annexin core domain and the model antigen ovalbumin (Anx-OVA) leads to strongly enhanced CD4+ T cell activation compared to incubation with the antigen OVA alone. A) Schematic presentation of the experiment. Murine bone marrow derived DC were incubated with OVA or Anx-OVA. CD4+ T cell activation was detected using CD4+ OT-II T cells that carry a transgenic T cell receptor specific for the OVA-derived ISQAVHAAHAEINEAGR (SEQ ID NO: 5) peptide, T cell activation was detected by secretion of Interleukin-2 (IL-2). B) Murine bone marrow derived DC were incubated with equal amounts of OVA or Anx-OVA. After 12 h of incubation, DC were co-cultured for 1 day with OT-II T cells. OT-II T cell activation was detected by measuring IL-2 secretion in ELISA.

FIG. 4 shows that incubation of DC (OVA-derived peptide SIINFEKL (SEQ ID NO: 4) within MHC I molecules on DC) with a fusion protein containing the annexin core domain and the model antigen ovalbumin (Anx-OVA) leads to strongly enhanced CD4+ T cell activation compared to incubation with the antigen OVA alone. A) Schematic presentation of the experiment. Murine bone marrow derived DC were incubated with OVA or Anx-OVA. CD4+ T cell activation was detected using CD4+ OT-II T cells that carry a transgenic T cell receptor specific for the OVA-derived ISQAVHAAHAEINEAGR (SEQ ID NO: 5) peptide, T cell activation was detected by secretion of Interferon-γ (IFN-γ). B) Murine bone marrow derived DC were incubated with equal amounts of OVA or Anx-OVA. After 12 h of incubation, DC were co-cultured for further 3-5 days with OT-II T cells. OT-II T cell activation was detected by measuring IFN-γ secretion in ELISA.

FIG. 5 shows that various annexins bind to the receptor LRP-1 with high affinity. Binding of the indicated recombinant annexins and the annexin A1 core domain to immobilized LRP-1 was detected by quartz crystal microbalance. Recombinant annexins were analyzed at 3 different concentrations. Depicted are fitted binding curves of the indicated annexins and the annexin A1 core domain to LRP-1. The calculated affinities for all annexins and the core annexin A1 domain range from 50-300 nM. Murine annexin A1 (mAnxA1): filled circles; murine annexin A1 core domain (mAnxA1 core): open circles; murine annexin A5 (mAnxA5): filled squares; murine annexin A13 (mAnxA13): open squares.

FIG. 6A shows an analysis of the binding of recombinant annexin A1 (Annexin I) and annexin A5 (Annexin V) to the indicated, immobilized C-type lectin molecules in ELISA.

Figure 1A:
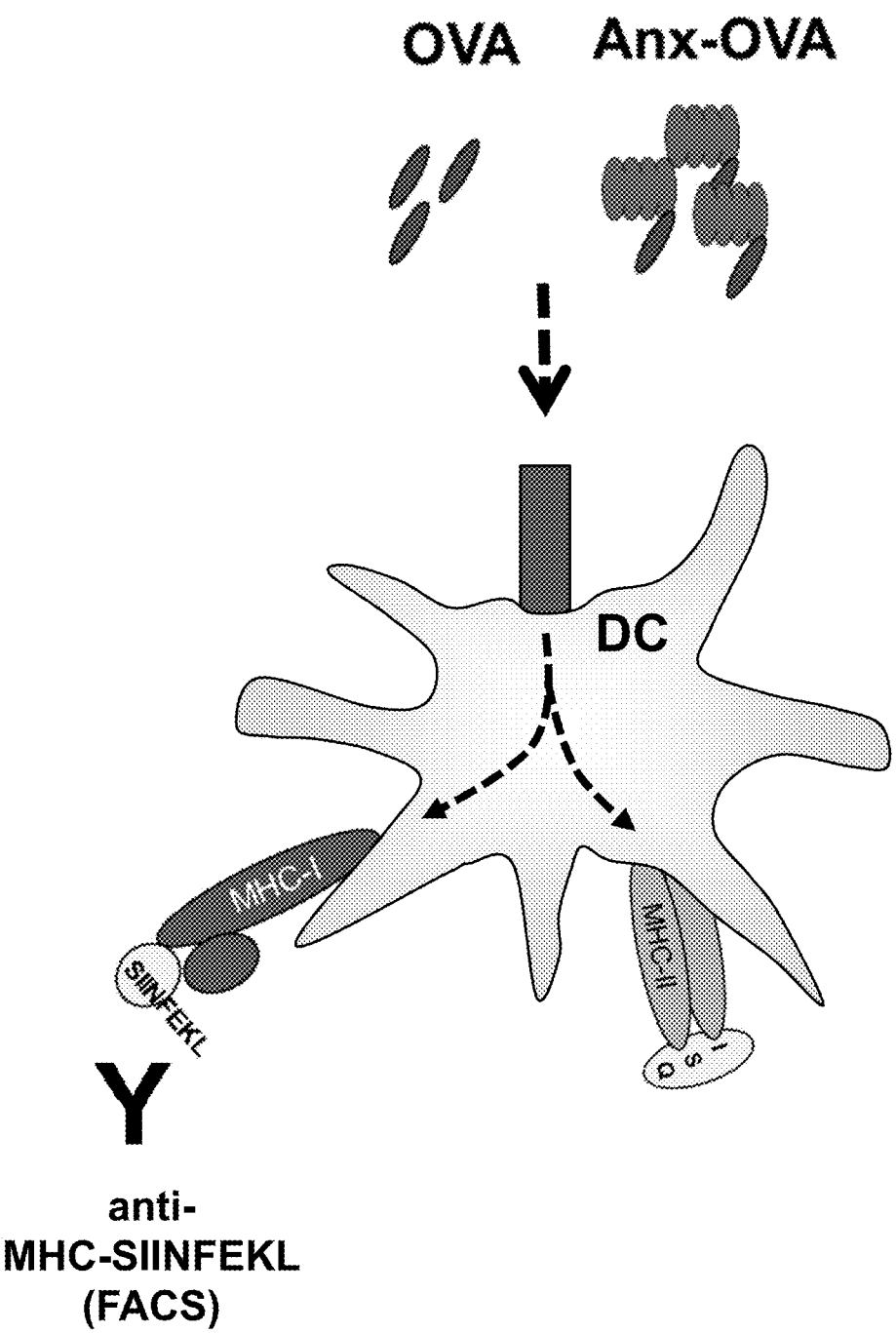
Figure 1B:
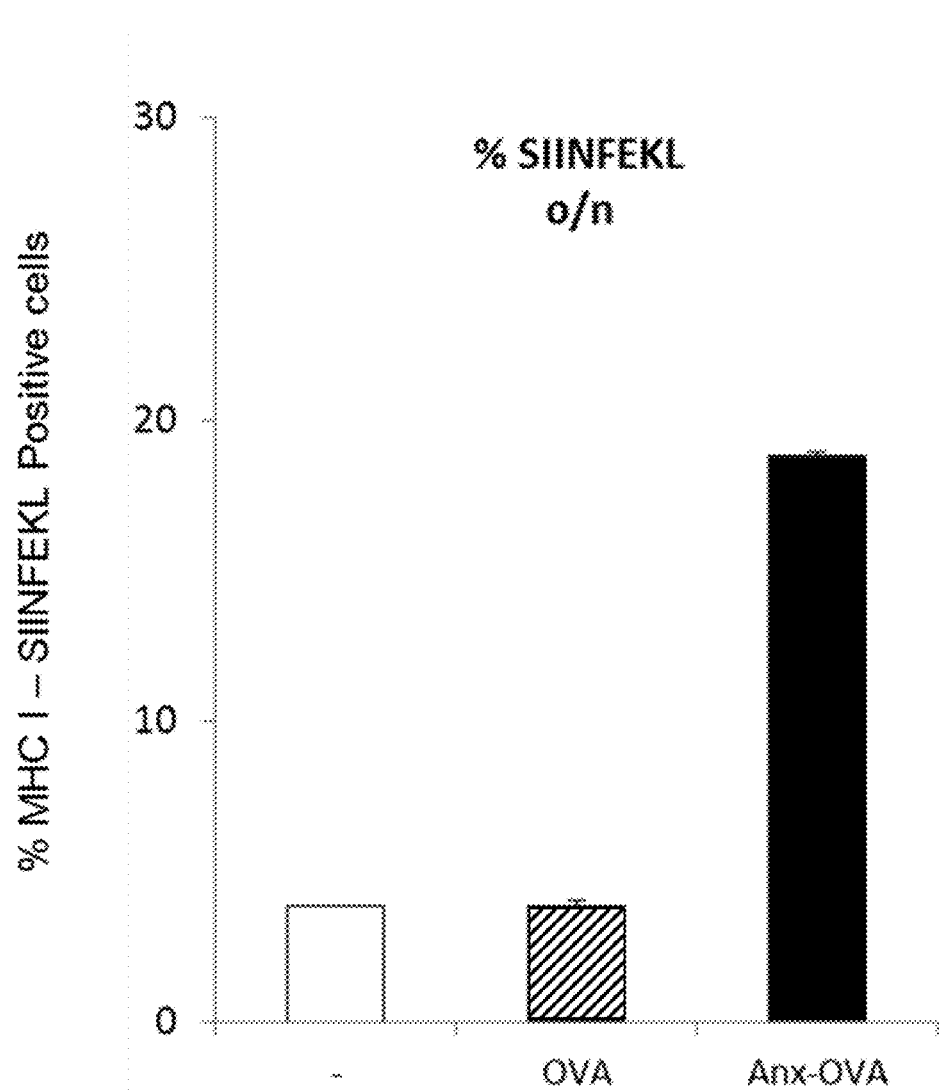
Figure 2A:
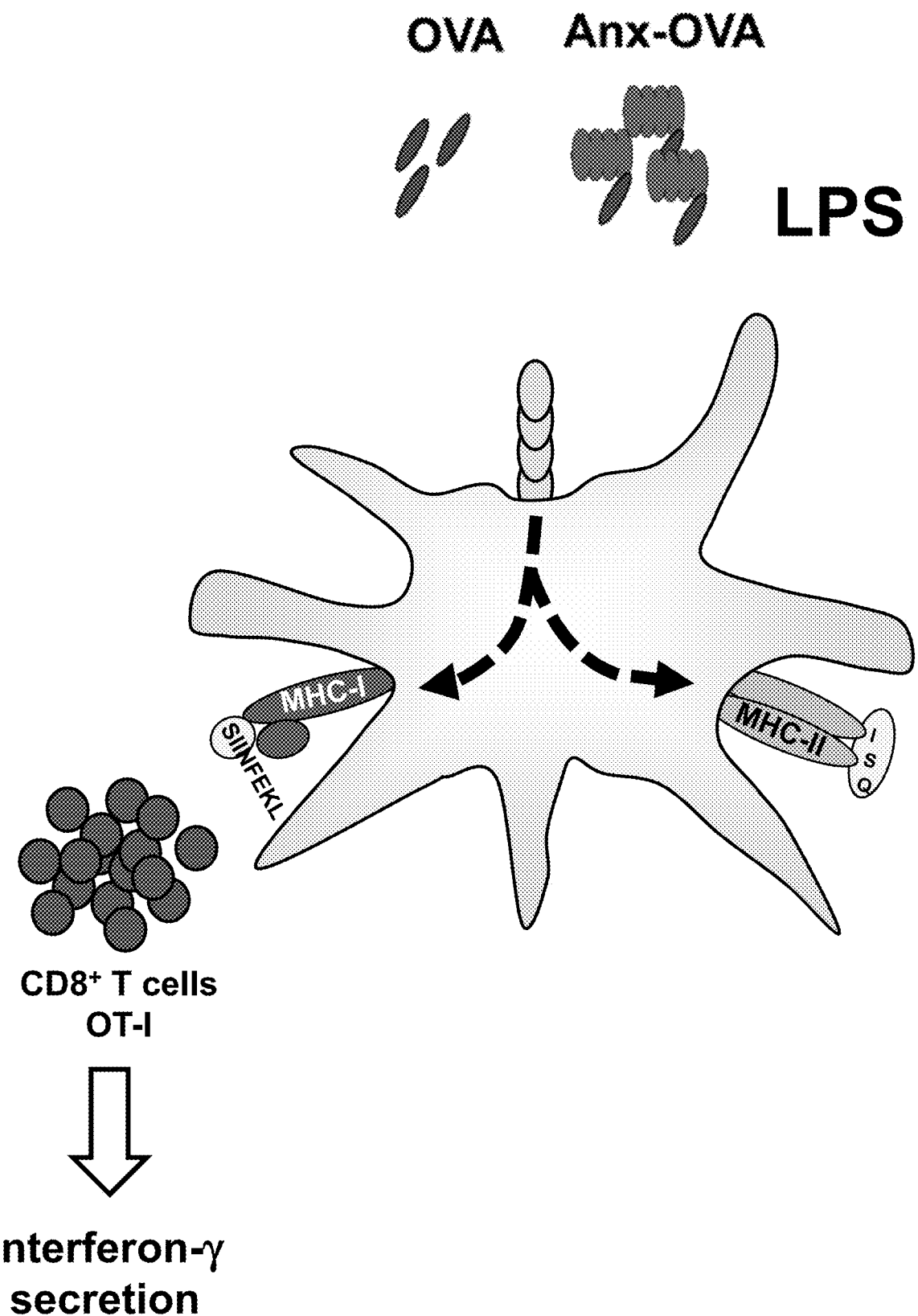
Figure 2B:
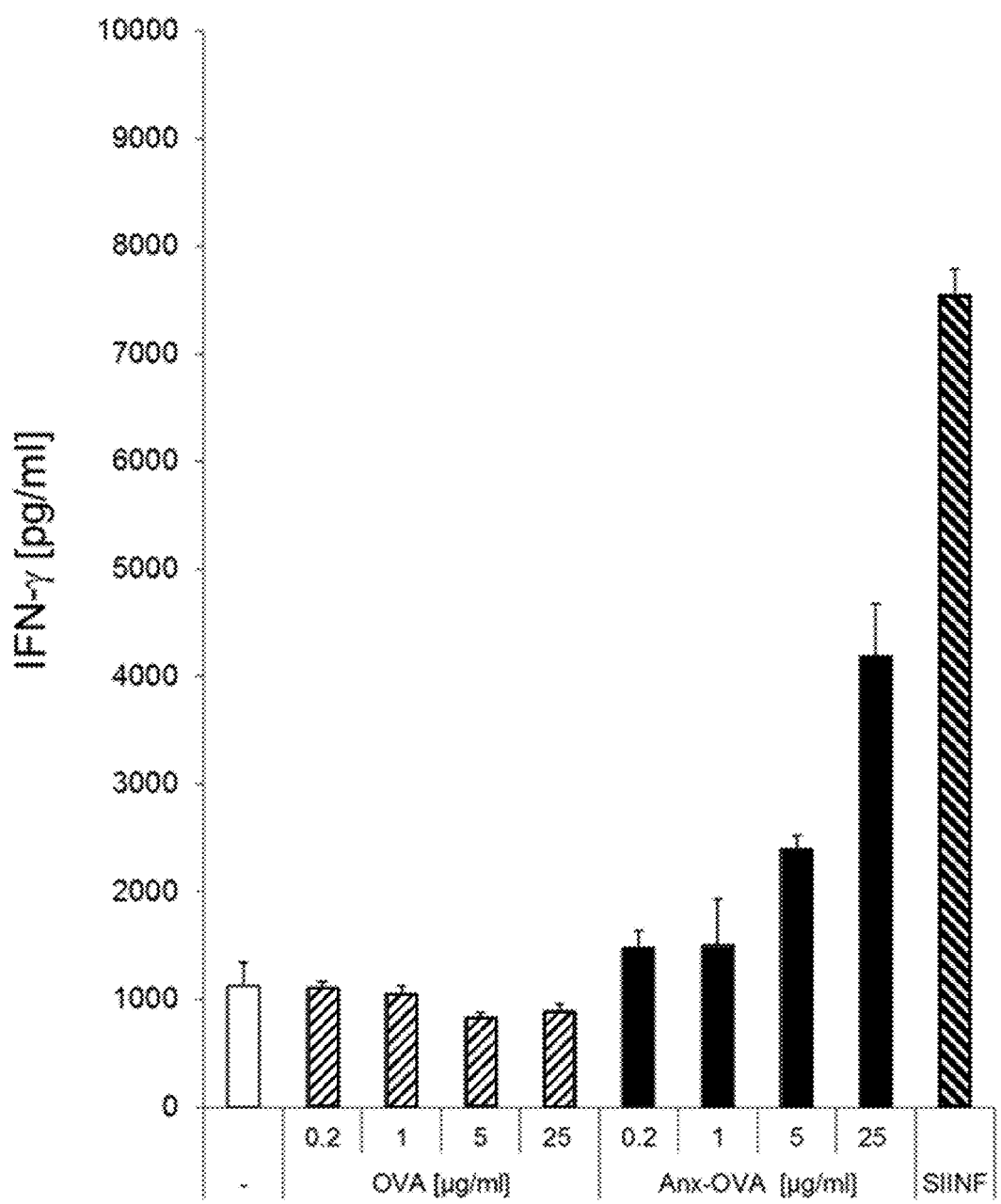
Figure 3A:
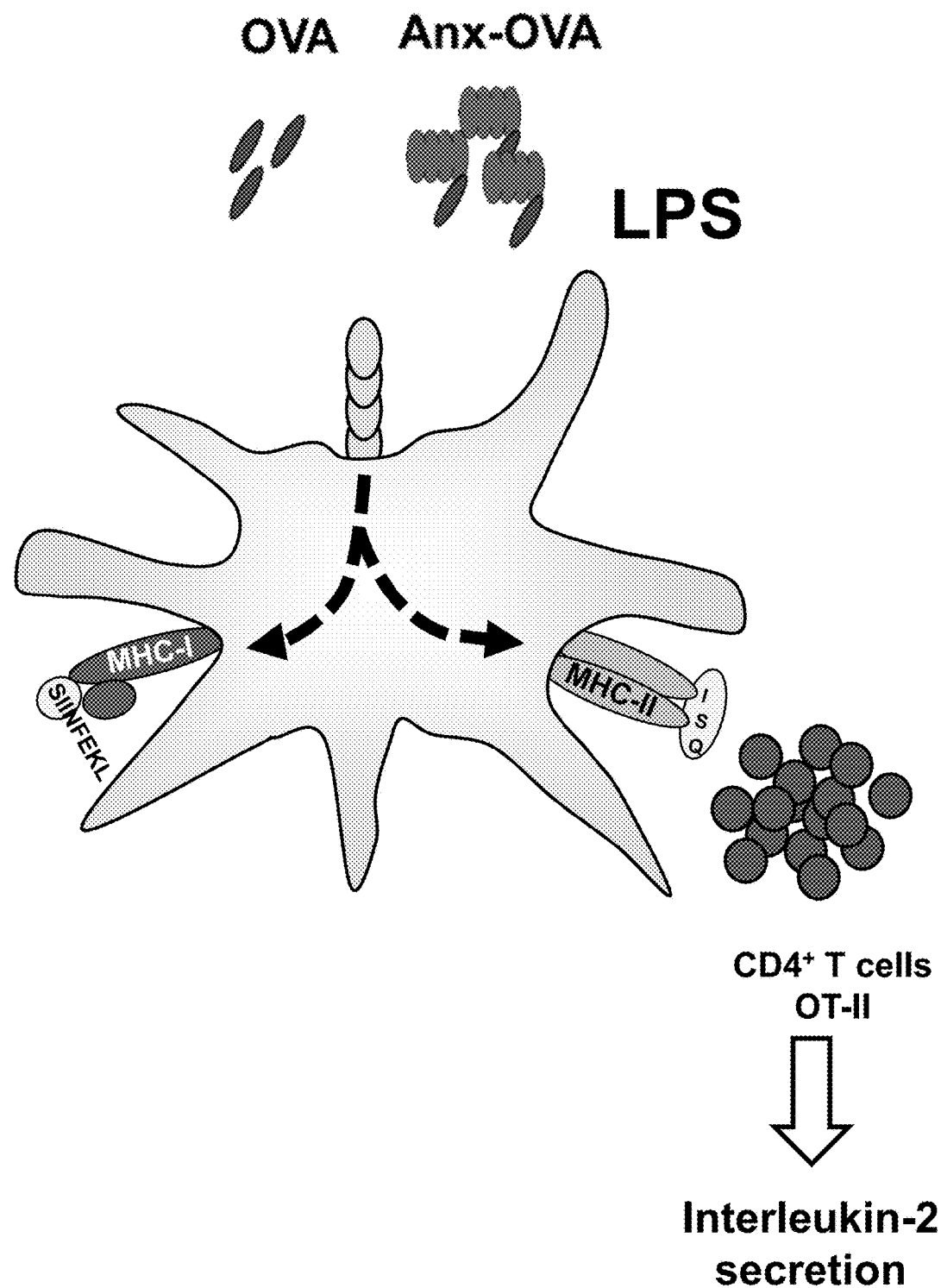
Figure 3B:
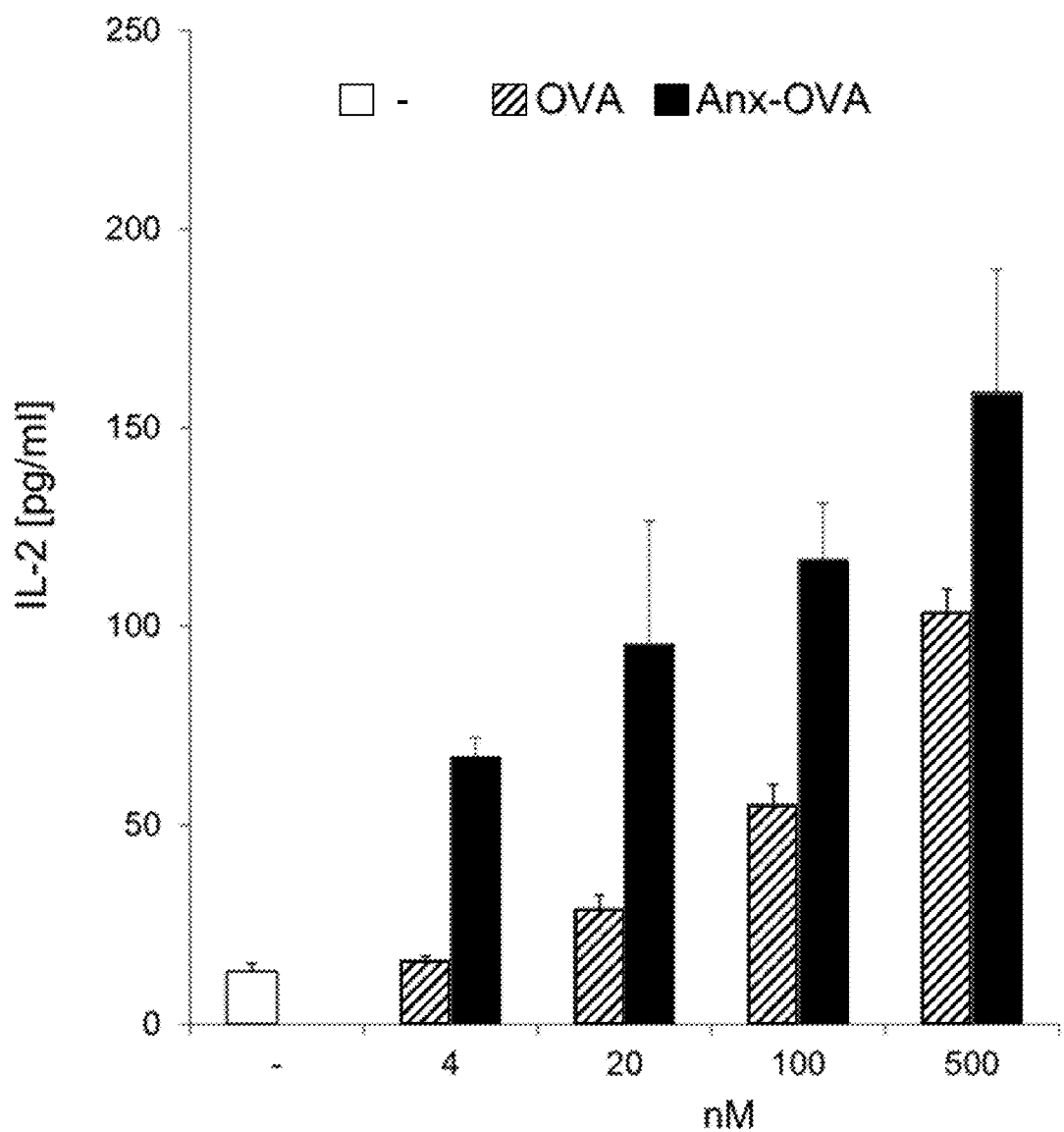
Figure 4A:
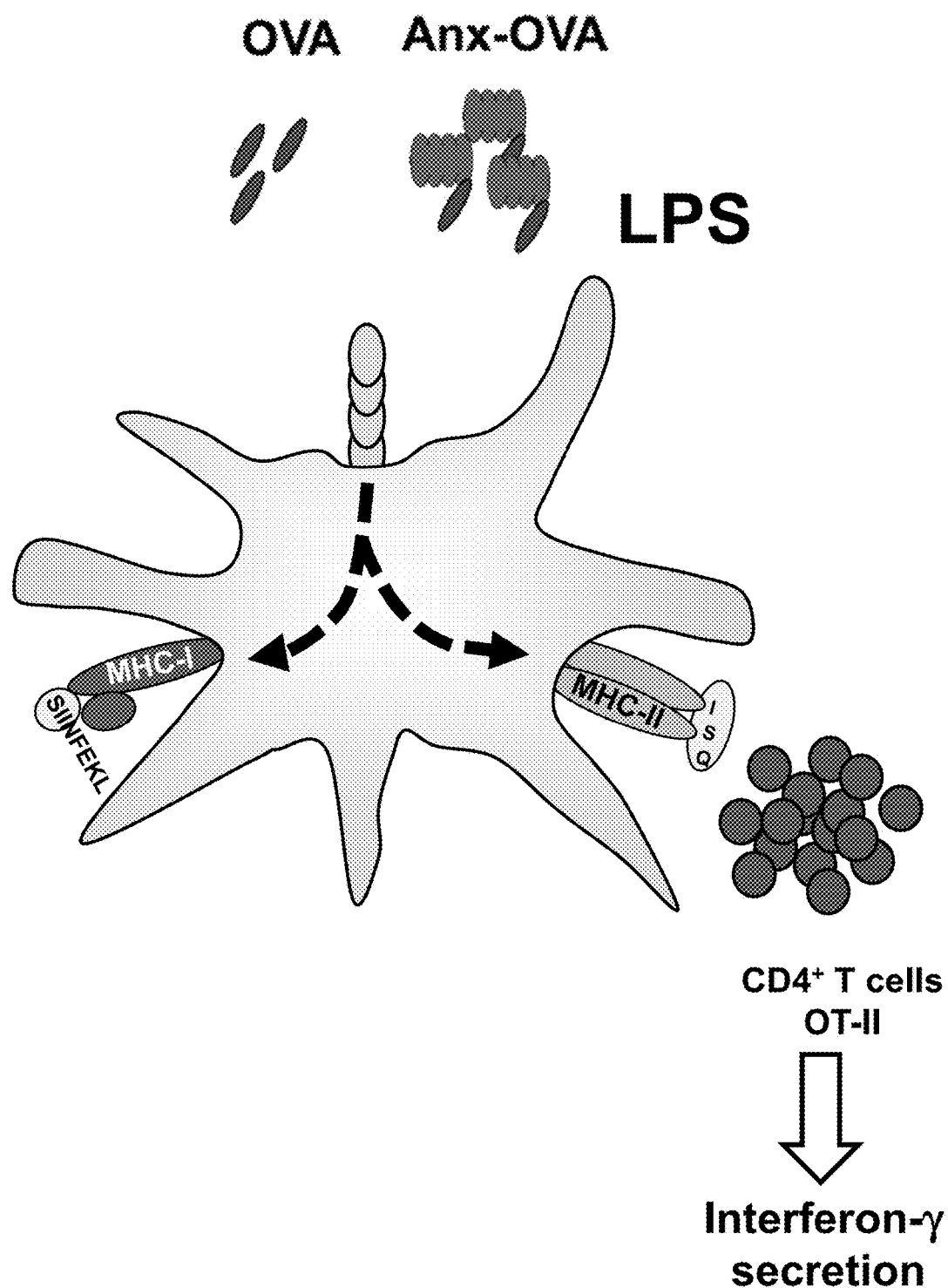
Figure 4B:
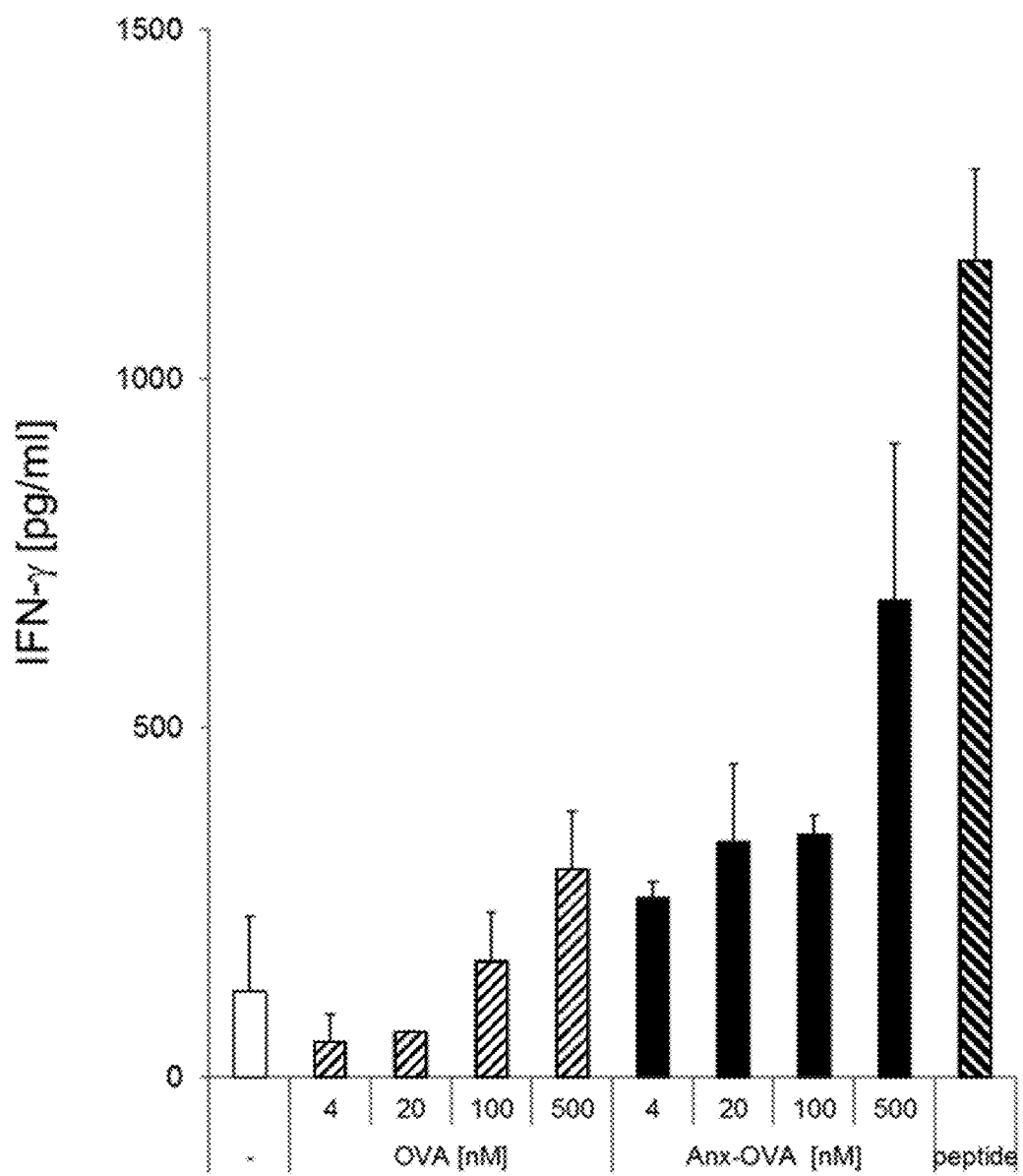
Figure 5:
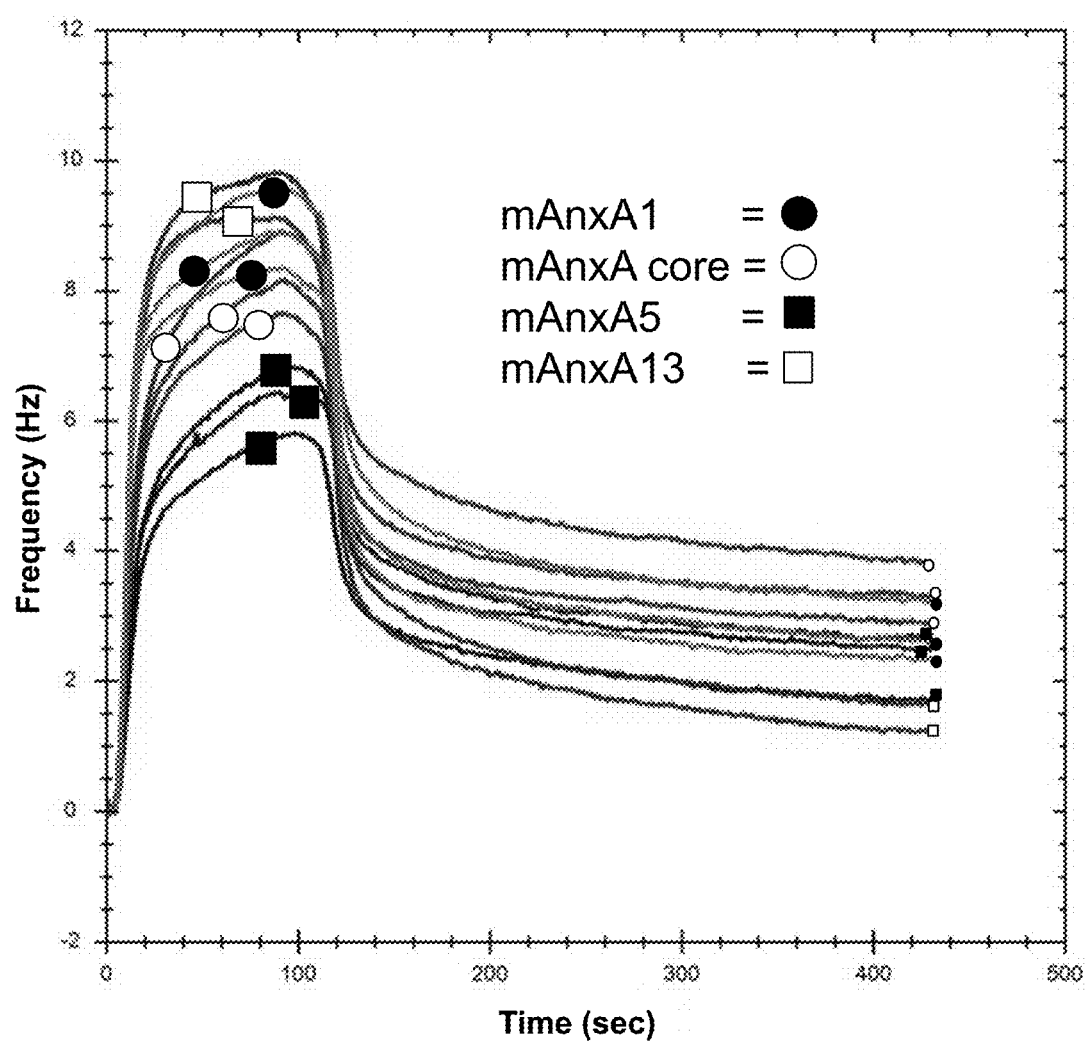
Figure 6A:
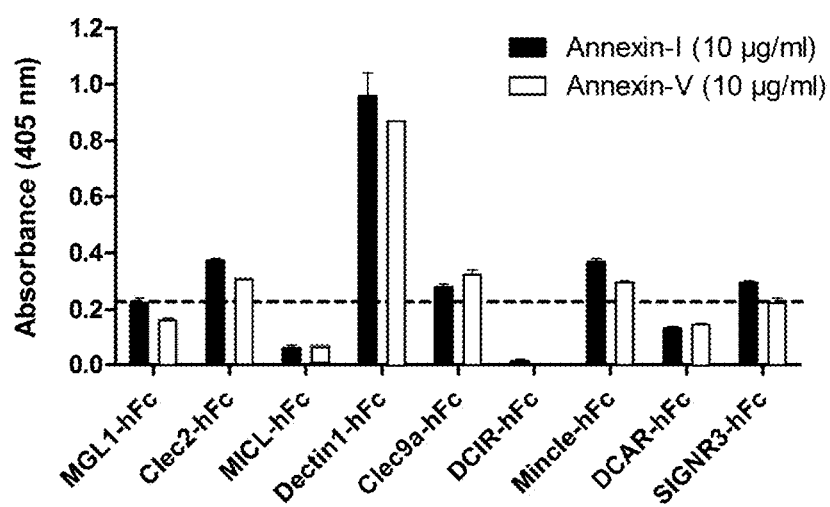
FIGS. 6A and 6B show that several annexins bind to the receptor Dectin-1 with high affinity.
Figure 6B:
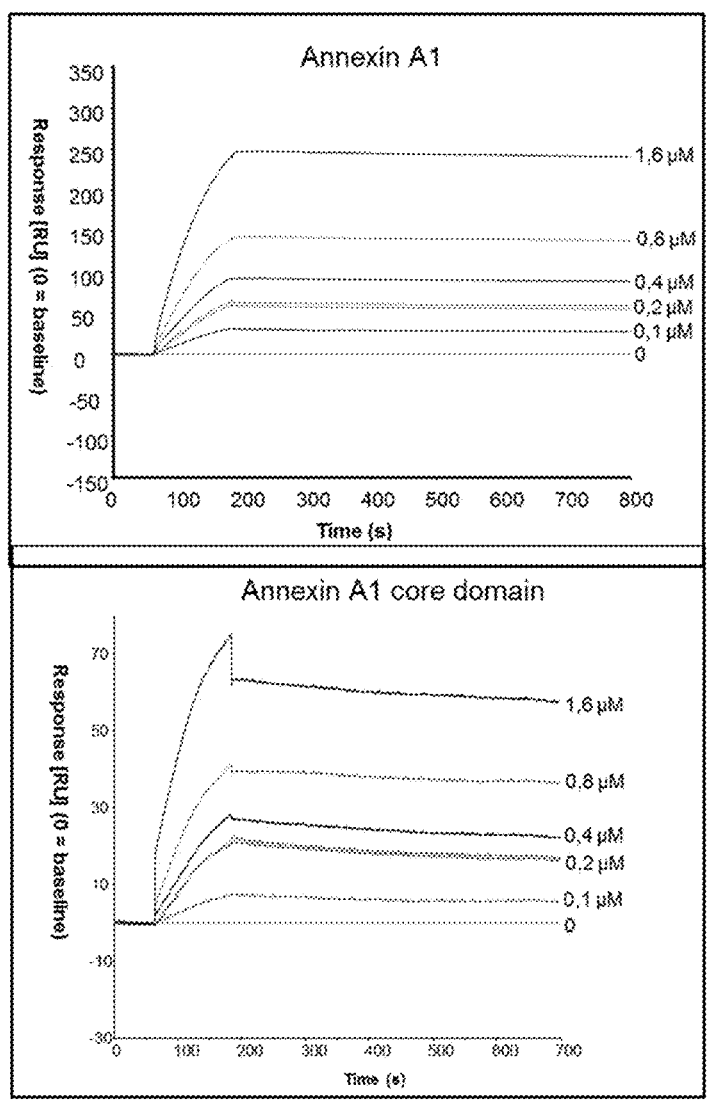
Figure 6B:
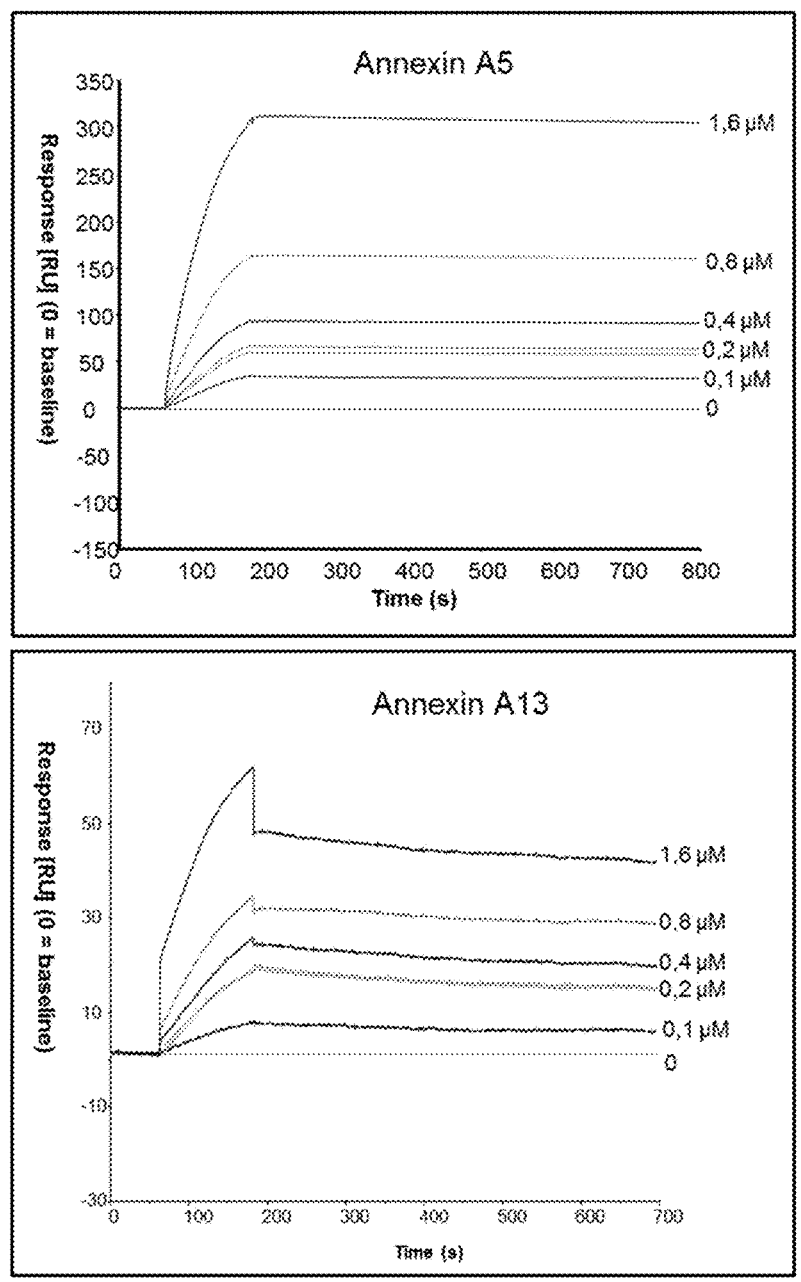

FIG. 6B shows surface plasmon resonance spectroscopy sensorgrams of the binding of murine annexin A1, annexin A5, annexin A13 and the annexin A1 core domain to the surface molecule Dectin-1. The indicated concentrations of the indicated recombinant annexins were allowed to bind to immobilized Dectin-1 and bound molecules were measured by surface plasmon resonance. Annexin affinities to Dectin-1 were calculated to be in the nanomolar range (~100 nM).

Figure 7:
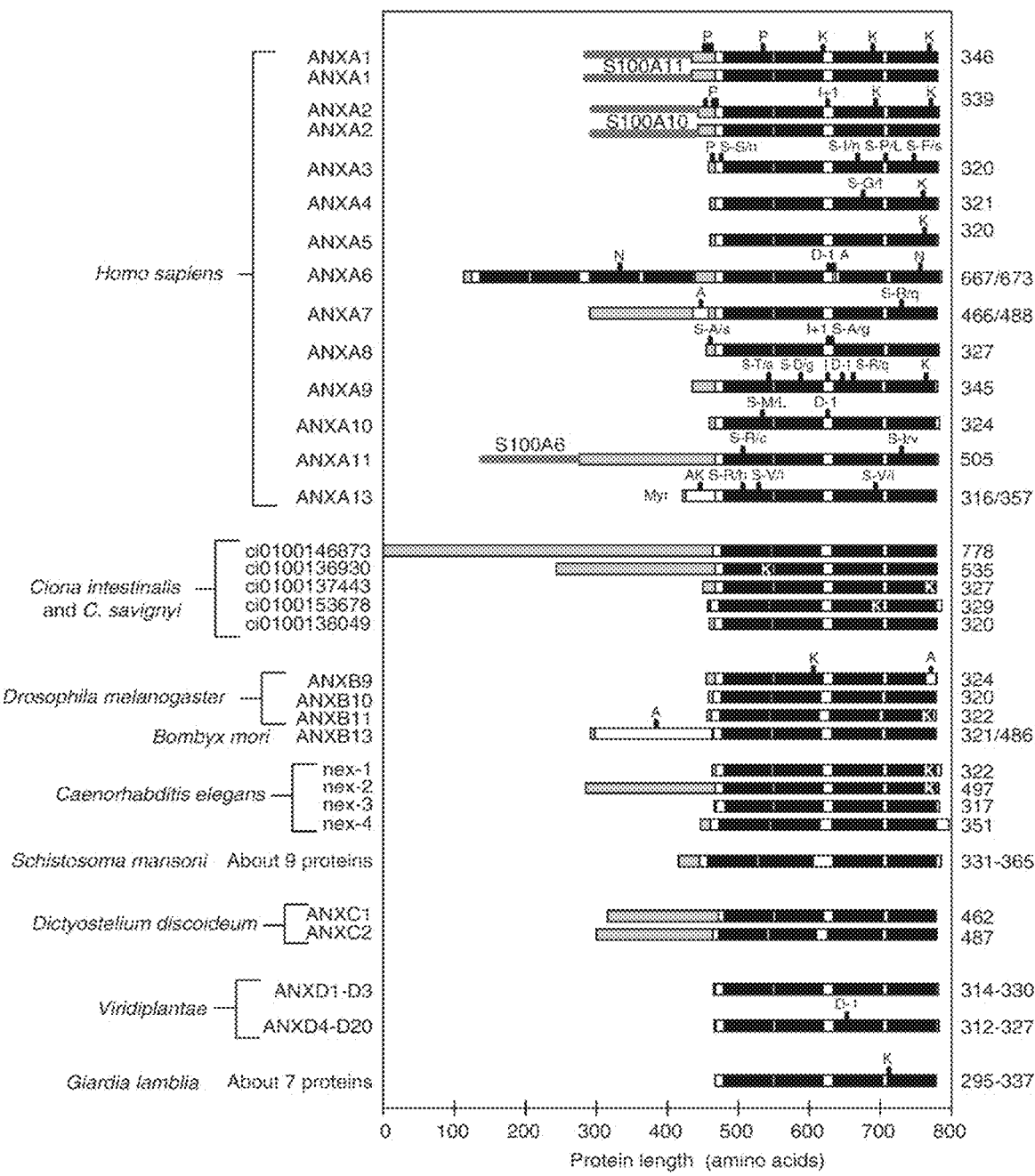

FIG. 7 shows the domain structures of representative annexin proteins. Orthologs of the 12 human annexins shown in other vertebrates have the same structures, with strict conservation of the four repeats in the core region (black) and variation in length and sequence in the amino-terminal regions (shaded). Human ANXA1 and ANXA2 are shown as dimers, with the member of the S100 protein family that they interact with. Domain structures for other model organisms are derived from public data made available by the relevant genome-sequencing projects. Features: S100Ax, sites for attachment of the indicated member of the S100 family of calcium-binding proteins; P, known phosphorylation sites; K, KGD synapomorphy (a conserved, inherited characteristic of proteins); I, codon insertions (+x denotes the number of codons inserted); S-A/b, nonsynonymous coding polymorphisms (SNPs) with the amino acid in the major variant (A) and that in the minor variant (b); N, putative nucleotide-binding sites; D, codon deletions (-x denotes the number of codons deleted); A, alternatively spliced exons; Myr, myristoylation. The total length of each protein is indicated on the right. Taken from Moss and Morgan. The annexins. Genome Biol. 2004; 5(4): 219.

FIG. 8 shows the accession numbers in FASTA format and an alignment of the protein sequences of human and murine annexins A1, A5 and A13. The sequence identifiers are as follows for the respective sequences.

GI I 47115305 I emb I CAG28612.1 I (hANXA1): SEQ ID NO: 1
GI I 49456639 I emb I CAG46640.1 I (hANXA5): SEQ ID NO: 2
GI I 49456633 I emb I CAG46637.1 I (hANXA13): SEQ ID NO: 3
GI I 71059925 I emb I CAJ16506.1 I (hANXA1): SEQ ID NO: 6
GI I 13277612 I gb I AAH03716.1 I (hANXA5): SEQ ID NO: 7
GI I 13397933 I emb I CAC34623.1 I (hANXA13): SEQ ID NO: 8.

The conserved sequence of the core domain of the annexins is boxed. An * (asterisk) indicates positions which have a single, fully conserved residue. A: (colon) indicates conservation between groups of strongly similar properties. A. (period) indicates conservation between groups of weakly similar properties.

Figure 9A:
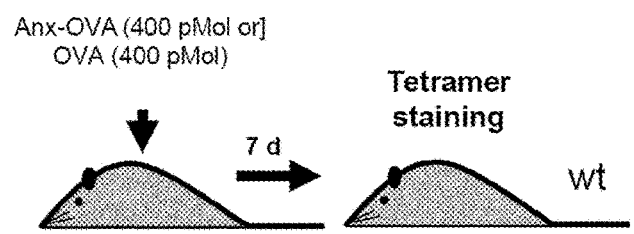
Figure 9B:
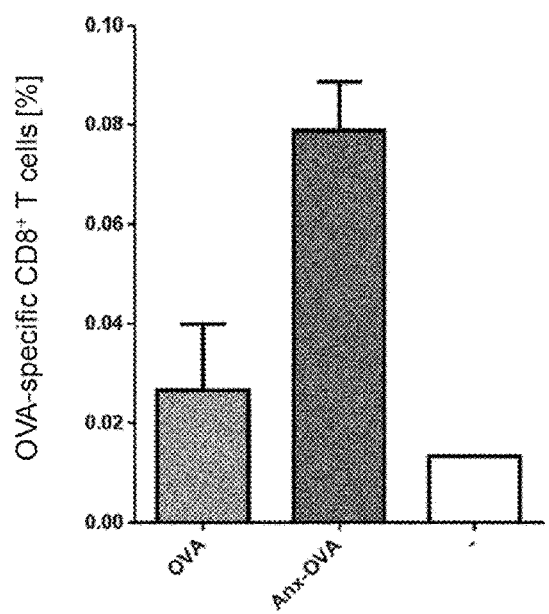
Figure 9C:
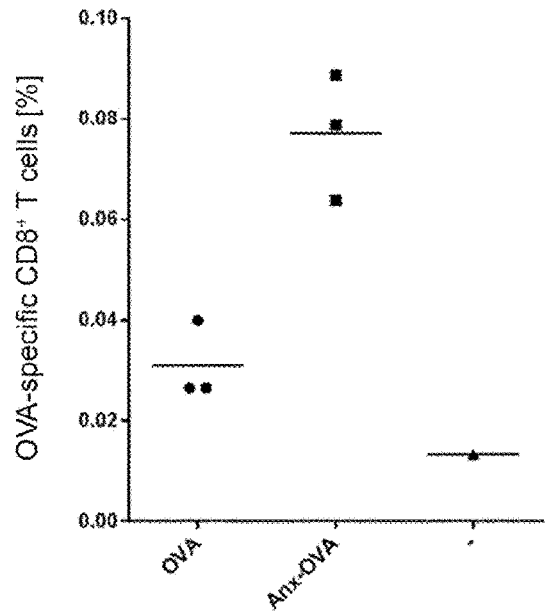

FIG. 9 demonstrates that vaccination with a fusion protein containing the annexin core domain and the model antigen ovalbumin (Anx-OVA) strongly improves vaccination efficacy compared to antigen OVA alone. A) Schematic presentation of the experiment. C57BL/6 wt mice were immunized with 400 pMol OVA or Anx-OVA per animal. Induction of antigen (OVA)-specific CD8+ T cells was detected 7 days after vaccination using fluorescently labeled SIINFEKL(SEQ ID NO: 4)-MHC class I tetramers. B) and C) Results indicating the frequency of OVA-specific CD8+ T cells within all CD8+ T cells after indicated vaccinations as average of 3 mice per group (B) and for each animal individually (C). OVA: ovalbumin, Anx-OVA: Fusionsprotein containing the annexin core domain, a linking sequence and ovalbumin, -: no vaccination FIG. 9B and FIG. 9C show results indicating the frequency of OVA-specific CD8+ T cells within all CD8+ T cells after indicated vaccinations as average of 3 mice per group (B) and for each animal individually (C). OVA: ovalbumin, Anx-OVA: Fusionsprotein containing the annexin core domain, a linking sequence and ovalbumin, -: no vaccination FIGS. 10A and 10B show the DNA-sequence [SEQ ID NO: 13] (A) and amino acid sequence [SEQ ID NO: 14] (B) of the Anx-OVA fusionprotein used for vaccination. light grey shading: human Annexin A1-core domain; no shading: linker sequence; dark grey shading: ovalbumin (OVA).

SEQ ID Nos. 1 to 3 and 6 to 8 show the sequences of the human and mouse annexin 1, 5, and 13, respectively, as used in the context of the present invention.

SEQ ID Nos. 4 and 5 show peptide sequences as used in the context of the present invention.

SEQ ID Nos: 9 to 12 show primer sequences as used in the present invention.

EXAMPLES

Sequences
The sequences are as follows:

| SeqID | UniProt Protein ID | Range | referred to in the text |
|---|---|---|---|
| 1 | P04083 | 41-344 | human Annexin A1 core domain |
| 2 | P08758 | 14-317 | human Annexin A5 core domain |
| 3 | P27216 | 13-316 | human Annexin A13 core domain |
| 4 | P01012 | 257-267 | ova peptide SIINFEKL |
| 5 | P01012 | 323-339 | ova peptide ISQAVHAAHAEINEAGR |
| 6 | P10107 | 41-344 | murine Annexin A1 core domain |
| 7 | P48036 | 12-315 | murine Annexin A5 core domain |
| 8 | Q99JG3 | 14-317 | murine Annexin A13 core domain |

Mice.

C57BL/6 mice were purchased from the Jackson Laboratory. All mice were maintained in specific-pathogen-free facilities.

Cells.

For differentiation of BM precursors to BMDCs using recombinant murine GM-CSF, 1×10⁶ cells were seeded at a density of 1×10⁶ cells/ml in RPMI 1640 complete medium (10% FCS, 10 U/ml penicillin/streptomycin, 300 mg/l L-glutamine, 20 ng/ml GM-CSF (Immunotools)) in a 24-well plate. After 2 days the medium was replaced by fresh medium. After 4 d, half of the medium was removed and replaced by fresh medium. Experiments were conducted 7-8 d after differentiation.

Generation of Recombinant Core Domain-Antigen Fusionprotein.

The mouse (m)AnxA1-OVA-pET41a plasmid was generated by cloning chicken Ovalbumin (OVA; NM_205152 or NP_990483, respectively, from amino acid 140) into a modified version of pET41a harboring a C-terminal FLAG tag, a PreScission Protease cleavage site, and a protein A tag. In addition, two flexible linkers and a Tobacco Etch Virus (TEV) cleavage site were introduced between mAnxA1 and OVA. Successive PCRs were performed using the following primers:

```
                                        (SEQ ID NO: 9)
Fw_1: 5'GGCGGAGGTTCAGGCGGAGGTTCA
GATCAAGCCAGAGAGCTCATC 3';

(SEQ ID NO: 10)
Fw_2: 5' GAAAACTTGTATTTCCAGGGCGGCGG
AGGTTCAGGCG 3'; , (SEQ ID NO: 11)
Fw_3: 5' GGATCCGGCGGAGGTTCAGGCGGAGGTT
CAGAAAACTTGTATTTCCAGGGCGG 3' and (SEQ ID NO: 12)
Rev: 5' GGATCCAGGGGAAACACATCTGCCAAAG 3'.
```

The final PCR product was subcloned using the pGEM®-T easy vector system from Promega. *Escherichia coli* BL21(DE3)pLysS strain (Promega) was used to express the fusionprotein. Overnight cultures of *E. coli* transformed with the vector described above were used to inoculate 4 L of LB containing 50 µg/ml kanamycin and 34 µg/ml chloramphenicol. Cultures were agitated at 180 rpm until A600 nm reached 0.6. Expression was induced using 1 mM isopropyl-D-thiogalactopyranoside (IPTG) for 4 hrs at 37° C. Cells were harvested by centrifugation and stored frozen at −20° C. Cell pellets containing Protein A-tagged recombinant fusion protein were resuspended in native bacterial lysis buffer and disrupted by six cycles of freeze and thaw. Cell extract was loaded onto IgG Sepharose 6 Fast Flow beads (GE Healthcare). Removal of LPS was achieved by washing with TBS containing 0.1% Triton X-114 (Sigma-Aldrich) as described previously (Reichelt, Schwarz et al. 2006, Zimmerman, Petit Frere et al. 2006). Triton X-114 was removed by washing with TBS containing 0.05% Tween-20. After cleavage of the fusion protein with PreScission Protease (GE Healthcare) and removal of PreScission Protease using Glutathione Sepharose Beads 4B (Amersham Biosciences), the recombinant protein was dialyzed against PBS. After sterile filtration, protein concentration was measured using BCA-Assay (Pierce) and LPS-content was determined using Limulus Amoebocyte Lysate Assay (Lonza).

Recombinant proteins were expressed in the *Escherichia coli* BL21(DE3)pLysS strain (Promega) from the pET41a vector (Novagen). PCR products encoding a fusionprotein of the annexin A1 core domain and full length chicken ovalbumin were cloned into pET41a harboring a C-terminal FLAG_tag, a PreScission protease cleavage site and a Protein A_tag. Bacterial lysates (10,000×g, 4° C. for 40 min) were loaded onto pre-equilibrated IgG Sepharose 6 Fast Flow beads (GE Healthcare). Removal of LPS was achieved by washing with TBS containing 0.1% Triton X-114 (Sigma). Triton X_114 was removed by washing with TBS containing 0.05% Tween-20 (Gerbu). After cleavage of the fusion protein with PreScission protease (GE Healthcare) and PreScission protease removal, the recombinant protein was dialysed against PBS. LPS content in all annexin A1 preparations was determined to be below 5 EU/mg using the Limulus Amoebocyte Lysate Assay (Lonza) according to the manufacturers' instructions.

Detection of Antigen Presentation In Vitro.

2×10⁵ BMDCs from C57BL/6 wildtype mice were incubated with 500 nM or the indicated amount of recombinant Ovalbumin (OVA, Sigma) or annexin core domain-OVA fusionprotein. After 8-12 h, DC were washed with PBS and incubated with a fluorescently labeled antibody against the OVA-derived peptide SIINFEKL (SEQ ID NO: 4) in MHC class I (antibody 25-D1.16, eBioscience). SIINFEKL(SEQ ID NO: 4)-positive cells were detected in FACS (FACS-Canto, BectonDickinson).

Coculture of DC and T Cells and T Cell Activation.

2×10⁵ BMDCs from C57BL/6 wildtype mice were incubated with 500 nM or the indicated amount of recombinant Ovalbumin (OVA,Sigma) or annexin core domain-OVA fusionprotein. After 12 h, 1×10⁶ magnetically purified (Easysep, Stemcell Technologies) CD8+ or CD4+ T cells from spleens of OT-I or OT-II mice, respectively, were added to the DC cultures. After 1-2 days (Interleukin-2) or 3-5 days (Interferon-γ) indicated cytokines were determined in the culture supernatants by ELISA (Becton-Dickinson).

Measuring the Affinity of the Binding Between Annexin and LRP-1.

For measuring the affinity of the binding of LRP-1 to different annexins (annexin A1, A5, and A13) the device A100 (ATTANA) was used. LRP-1 was immobilized on an LNB carboxychip according to the manufacturers' instructions. In order to achieve this, first, the chip was activated with EDC/SulfoNHS according to the manufacturers' instructions, and then purified LRP1 (5-15 µg/ml) in a sodium acetate buffer (pH 4.0) was injected onto the chip until an increase of the frequency at 70-100 Hz was reached. Then, remaining binding spots on the chip were saturated using two injections of ethanolamine, and the chip was buffered in PBS. For the incubation with the different annexins, they were prepared in six different concentrations in PBS with 2 mM calcium, and measured in triplicates. After each Anx-injection the chip was regenerated with 5 mM EDTA/PBS and 3M NaCl before the next Anx-injection.

Annexin Binding Measurement for Different Receptors by ELISA.

To test for binding to annexins, putative receptor molecules, fragments thereof or fusion proteins (e.g. LRP-11, single LRP-1 domains or Dectin-1 Fc protein) are immobilized on an ELISA plate at 10 µg/ml in coating buffer (Carbonate-Bicarbonate—1.5 g $Na_2CO_3$; 2.93 g $NaHCO_3$; Distilled water, 1 liter, pH to 9.6). After washing (3×PBS Tween 0.01%) and blocking (1% Casein in PBS), different concentrations of recombinant annexins are incubated in the wells for 2 h, followed by 5 wash steps (PBS-Tween 0.05%). Bound annexins are then detected by suitable secondary reagents (e.g. horse radish peroxidase (HRP) labeled secondary antibodies or biotin-labeled secondary antibodies plus streptavidin-labeled HRP) to the recombinant annexin-proteins and measured by reactivity with a suitable substrate (e.g. OPD) in an ELISA plate reader. The assay can also be performed by immobilizing different annexins on a plate and probing with recombinant receptor molecules, fragments thereof or fusion proteins (e.g. LRP-11, single LRP-1 domains or Dectin-1 Fc protein).

Binding Affinity Measurements for Annexin—Dectin 1 by Surface Plasmon Resonance.

Surface plasmon resonance (SPR) is a valuable tool for analyzing receptor ligand interactions in real time and for providing insights into the affinity and kinetics of binding. SPR is a technique for measuring the association and dissociation kinetics of ligand, termed analyte, with a receptor. The analyte or the receptor can be immobilized on a sensor chip which bears a gold film. The association of the analyte and receptor with one or the other, depending which one is immobilized, induces a change in the refractive index of the layer in contact with the gold film. This is measured as a change in the refractive index at the surface layer and is recorded as the SPR signal in resonance units (RU). For the preparation of Dectin-1-coated surfaces, Dectin-1 was immobilized at a flow rate of 10 µl/min. The CMS chip was activated by injection of a mixture of N-ethyl-N'-(diethyl-aminopropyl)-carbodiimide (EDC) and N-hydroxysuccin-imide (NHS) for 10 minutes and functionalized by injecting 100 µg/mL and 10 µg/mL Dectin-1 in acetate buffer pH 5.5 for 7 minutes. The remaining activated carboxyl groups were then capped by injection of 1 M ethanolamine for 10 minutes. Control flow cells were treated with EDC/NHS followed by ethanolamine as described. Concentration gradients of the different annexins were injected over the Dectin-1-functionalized surfaces at 10 µL/min, allowing 60 seconds for contact and 300 seconds for dissociation times, followed by regeneration using 100 mM methyl-α-D-mannopyranoside at 30 µL/min for 30 seconds. Experimental data were analyzed using Biacore S20 T100 Evaluation Software. Kinetic analyses based on a 1:1 interaction model for the annexin-dectin-1 complexes interaction were performed using Scrubber2 (BioLogic Software, Campbell, Australia).

In FIGS. 9A-9C an in vivo experiment demonstrates that vaccination with a fusion protein containing the annexin core domain and the model antigen ovalbumin (Anx-OVA) strongly improves vaccination efficacy compared to antigen OVA alone.

REFERENCES AS CITED

Andersen, B. M., J. Xia, A. L. Epstein, J. R. Ohlfest, W. Chen, B. R. Blazar, C. A. Pennell and M. R. Olin (2016). "Monomeric annexin A2 is an oxygen-regulated toll-like receptor 2 ligand and adjuvant." *J Immunother Cancer* 4: 11.

Arur, S., U. E. Uche, K. Rezaul, M. Fong, V. Scranton, A. E. Cowan, W. Mohler and D. K. Han (2003). "Annexin I is an endogenous ligand that mediates apoptotic cell engulfment." *Dev Cell* 4(4): 587-598.

Buhrman, J D and J. E. Slansky (2013). "Improving T cell responses to modified peptides in tumor vaccines." *Immunol Res* 55(1-3): 34-47.

Emonard, H., L. Theret, A. H. Bennasroune and S. Dedieu (2014). "Regulation of LRP-1 expression: make the point." *Pathol Biol (Paris)* 62(2): 84-90.

Ernst, S., C. Lange, A. Wilbers, V. Goebeler, V. Gerke and U. Rescher (2004). "An annexin 1 N-terminal peptide activates leukocytes by triggering different members of the formyl peptide receptor family." *J Immunol* 172(12): 7669-7676.

Farber, S. A., R. A. De Rose, E. S. Olson and M. E. Halpern (2003). "The zebrafish annexin gene family." *Genome Res* 13(6A): 1082-1096.

Fatimathas, L and S. E. Moss (2010). "Annexins as disease modifiers." *Histol Histopathol* 25(4): 527-532.

Gerke, V. and S. E. Moss (2002). "Annexins: from structure to function." *Physiol Rev* 82(2): 331-371.

Grakoui, A., S. K. Bromley, C. Sumen, M. M. Davis, A. S. Shaw, P. M. Allen and M. L. Dustin (1999). "The immunological synapse: a molecular machine controlling T cell activation." *Science* 285(5425): 221-227.

Hayhoe, R. P., A. M. Kamal, E. Solito, R. J. Flower, D. Cooper and M. Perretti (2006). "Annexin 1 and its bioactive peptide inhibit neutrophil-endothelium interactions under flow: indication of distinct receptor involvement." *Blood* 107(5): 2123-2130.

Kambayashi, T. and T. M. Laufer (2014). "Atypical MHC class II-expressing antigen-presenting cells: can anything replace a dendritic cell?" *Nat Rev Immunol* 14(11): 719-730.

Ling, T. Y., C. L. Chen, Y. H. Huang, I. H. Liu, S. S. Huang and J. S. Huang (2004). "Identification and characterization of the acidic pH binding sites for growth regulatory ligands of low density lipoprotein receptor-related protein-1." *J Biol Chem* 279(37): 38736-38748.

Linke, B., L. Abeler-Dorner, V. Jahndel, A. Kurz, A. Mahr, S. Pfrang, L. Linke, P. H. Krammer and H. Weyd (2015). "The tolerogenic function of annexins on apoptotic cells is mediated by the annexin core domain" *J Immunol* 194(11): 5233-5242.

Lutz, M. B. (2016). "Induction of CD4(+) Regulatory and Polarized Effector/helper T Cells by Dendritic Cells." *Immune Netw* 16(1): 13-25.

Moss, S. E. and R. O. Morgan (2004). "The annexins." *Genome Biol* 5(4): 219.

Perretti, M. and J. Dalli (2009). "Exploiting the Annexin A1 pathway for the development of novel anti-inflammatory therapeutics." *Br J Pharmacol* 158(4): 936-946.

Pupjalis, D., J. Goetsch, D. J. Kottas, V. Gerke and U. Rescher (2011). "Annexin A1 released from apoptotic cells acts through formyl peptide receptors to dampen inflammatory monocyte activation via JAK/STAT/SOCS signalling" *EMBO Mol Med* 3(2): 102-114.

Reichelt, P., C. Schwarz and M. Donzeau (2006). "Single step protocol to purify recombinant proteins with low endotoxin contents." *Protein Expr Purif* 46(2): 483-488.

Segura, E. and S. Amigorena (2015). "Cross-Presentation in Mouse and Human Dendritic Cells." *Adv Immunol* 127: 1-31.

Strausbaugh, H. J. and S. D. Rosen (2001). "A potential role for annexin 1 as a physiologic mediator of glucocorticoid-induced L-selectin shedding from myeloid cells." *J Immunol* 166(10): 6294-6300.

Tzelepis, F., M. Verway, J. Daoud, J. Gillard, K. Hassani-Ardakani, J. Dunn, J. Downey, M. E. Gentile, J. Jaworska, A. M. Sanchez, Y. Nedelec, H. Vali, M. Tabrizian, A. S. Kristof, I. L. King, L. B. Barreiro and M. Divangahi (2015). "Annexin1 regulates DC efferocytosis and cross-presentation during *Mycobacterium tuberculosis* infection." *J Clin Invest* 125(2): 752-768.

Verboogen, D. R., I. Dingjan, N. H. Revelo, L. J. Visser, M. ter Beest and G. van den Bogaart (2016). "The dendritic cell side of the immunological synapse." *Biomol Concepts* 7(1): 17-28.

Walther, A., K. Riehemann and V. Gerke (2000). "A novel ligand of the formyl peptide receptor: annexin I regulates neutrophil extravasation by interacting with the FPR." *Mol Cell* 5(5): 831-840.

Weyd, H., L. Abeler-Dorner, B. Linke, A. Mahr, V. Jahndel, S. Pfrang, M. Schnolzer, C. S. Falk and P. H. Krammer (2013). "Annexin A1 on the surface of early apoptotic cells suppresses CD8+ T cell immunity" *PLoS One* 8(4): e62449.

Zimmerman, T., C. Petit Frere, M. Satzger, M. Raba, M. Weisbach, K. Dohn, A. Popp and M. Donzeau (2006). "Simultaneous metal chelate affinity purification and endotoxin clearance of recombinant antibody fragments." *J Immunol Methods* 314(1-2): 67-73.

The invention claimed is:

1. A protein conjugate or fusion protein comprising (i) at least one annexin core domain comprising an amino acid sequence of a core domain as comprised in a sequence selected from the group consisting of SEQ ID NOs: 1 to 3 and 6 to 8, or an amino acid sequence that is at least 90% identical to an amino acid sequence of an annexin core domain as comprised in a sequence selected from the group consisting of SEQ ID NOs: 1 to 3 and 6 to 8, and (ii) at least one antigenic peptide that is presented by MHC, wherein the at least one antigenic peptide is derived from a protein selected from the group consisting of prostate specific antigen (PSA); BAGE; GAGE; MAGE 2, 6 and 12; MUC-2, GM2 and GD2 gangliosides; ras; myc; tyrosinase; cyclin B1; cyclin D; GnT-V intron V sequence (N-acetylglucoaminyltransferase V intron V sequence); prostate Ca psm; PRAME (melanoma antigen); β-catenin; MUM-1-B (melanoma ubiquitous mutated gene product); EBNA (Epstein-Barr Virus nuclear antigen) 1-6; gp75; human papilloma virus (HPV) E6 and E7; p53; lung resistance protein (LRP); Bcl-2; Ki-67; papilloma virus; βCG; gp100 or Pmel17; HER2/neu; WT1; mesothelin; CEA; gp100; MART1; TRP-2; NY-BR-1; NY-CO-58; MN (gp250); idiotype, tyrosinase; telomerase; SSX2; MUC-1; MARTI; melan-A; NY-ESO-1; MAGE-1; MAGE-3; MAGE-A3; high molecular weight-melanoma associated antigen (HMW-MAA); and an OVA-derivative peptide that consists of an amino acid sequence of SEQ ID NO: 4.

2. The protein conjugate or fusion protein according to claim 1, wherein said conjugate or said fusion protein is further conjugated/fused to a co-stimulatory molecule or an immunogenic fragment thereof or a costimulatory second peptide sequence.

3. A pharmaceutical composition comprising the protein conjugate or fusion protein of claim 1, and a carrier.

4. The pharmaceutical composition according to claim 3, which is a vaccine.

5. A method for treating or preventing an infectious disease or cancer, comprising administering an effective amount of a pharmaceutical composition according to claim 3.

6. A method for treating or preventing an infectious disease or cancer in a subject comprising administering to said subject the pharmaceutical composition according to claim 3.

7. A nucleic acid encoding for the fusion protein according to claim 1.

8. The nucleic acid according to claim 7, wherein said coding sequence is fused to at least one DC-stimulatory nucleic acid sequence.

9. A recombinant expression vector expressing the nucleic acid according to claim 7.

10. A pharmaceutical composition comprising the expression vector according to claim 9, and a carrier.

11. A pharmaceutical composition comprising the nucleic acid according to claim 7, and a carrier.

* * * * *